(12) United States Patent
Dihora et al.

(10) Patent No.: US 10,188,593 B2
(45) Date of Patent: Jan. 29, 2019

(54) POLYSACCHARIDE DELIVERY PARTICLE

(71) Applicant: Spray-Tek, Inc., Middlesex, NJ (US)

(72) Inventors: Jiten Odhavji Dihora, Center Valley, PA (US); Caroline Rachel Multari, Bethlehem, PA (US)

(73) Assignee: Spray-Tek, Inc., Middlesex, NJ (US)

( * ) Notice: Subject to any disclaimer, the term of this patent is extended or adjusted under 35 U.S.C. 154(b) by 0 days.

(21) Appl. No.: 15/625,340

(22) Filed: Jun. 16, 2017

(65) Prior Publication Data

US 2017/0360676 A1    Dec. 21, 2017

Related U.S. Application Data

(60) Provisional application No. 62/351,597, filed on Jun. 17, 2016.

(51) Int. Cl.
| | | |
|---|---|---|
| *A61K 8/02* | (2006.01) | |
| *A61K 8/25* | (2006.01) | |
| *A61K 8/73* | (2006.01) | |
| *A61K 8/92* | (2006.01) | |
| *A61K 9/16* | (2006.01) | |
| *A61Q 5/02* | (2006.01) | |
| *A61Q 5/12* | (2006.01) | |
| *C09K 3/30* | (2006.01) | |
| *C11D 3/00* | (2006.01) | |
| *C11D 3/08* | (2006.01) | |
| *C11D 3/12* | (2006.01) | |
| *C11D 3/22* | (2006.01) | |
| *C11D 3/37* | (2006.01) | |
| *C11D 3/50* | (2006.01) | |
| *A01N 25/28* | (2006.01) | |
| *A23L 27/00* | (2016.01) | |
| *A61Q 13/00* | (2006.01) | |
| *A61Q 15/00* | (2006.01) | |
| *A61Q 19/00* | (2006.01) | |
| *A61Q 19/10* | (2006.01) | |
| *B01J 13/04* | (2006.01) | |
| *C11D 17/00* | (2006.01) | |
| *F28D 20/02* | (2006.01) | |

(52) U.S. Cl.
CPC ............ *A61K 8/732* (2013.01); *A01N 25/28* (2013.01); *A23L 27/72* (2016.08); *A61K 8/0241* (2013.01); *A61K 8/25* (2013.01); *A61K 8/922* (2013.01); *A61K 9/1652* (2013.01); *A61Q 5/02* (2013.01); *A61Q 5/12* (2013.01); *A61Q 13/00* (2013.01); *A61Q 15/00* (2013.01); *A61Q 19/007* (2013.01); *A61Q 19/10* (2013.01); *B01J 13/043* (2013.01); *C11D 3/001* (2013.01); *C11D 3/08* (2013.01); *C11D 3/124* (2013.01); *C11D 3/222* (2013.01); *C11D 3/3723* (2013.01); *C11D 3/3769* (2013.01); *C11D 3/505* (2013.01); *C11D 17/0039* (2013.01); *A61K 2800/31* (2013.01); *A61K 2800/60* (2013.01); *C09K 3/30* (2013.01); *F28D 20/023* (2013.01)

(58) Field of Classification Search
CPC ............ A61K 2800/31; A61K 2800/60; A61K 8/0241; A61K 8/25; A61K 8/732; A61K 8/922; A61K 9/1652; A61Q 13/00; A61Q 15/00; A61Q 19/007; A61Q 19/10; A61Q 5/02; A61Q 5/12; C11D 3/001; C11D 17/0039; C11D 3/08; C11D 3/124; C11D 3/222; C11D 3/3723; C11D 3/3769
See application file for complete search history.

(56) References Cited

U.S. PATENT DOCUMENTS

| | | |
|---|---|---|
| 3,345,358 A | 10/1967 | Inklaar |
| 3,819,838 A | 6/1974 | Smith et al. |
| 5,550,189 A | 8/1996 | Qin et al. |
| 6,572,919 B2 | 6/2003 | Westland et al. |
| 8,900,495 B2 | 12/2014 | Pacorel et al. |
| 2004/0033264 A1* | 2/2004 | Sawhney ............ A61K 9/1647 424/486 |
| 2005/0272628 A1 | 12/2005 | Meli et al. |
| 2005/0276831 A1* | 12/2005 | Dihora .................. A61K 8/11 424/401 |
| 2009/0209661 A1 | 8/2009 | Somerville Roberts et al. |
| 2011/0268802 A1* | 11/2011 | Dihora .................. A61K 8/11 424/489 |
| 2013/0022654 A1* | 1/2013 | Deshmukh .......... A61K 9/0004 424/400 |
| 2014/0335032 A1 | 11/2014 | Panandiker et al. |

FOREIGN PATENT DOCUMENTS

| | | |
|---|---|---|
| EP | 1797946 A2 | 6/2007 |
| WO | 9901214 A1 | 1/1999 |
| WO | 0105926 A1 | 1/2001 |
| WO | 2007135583 A2 | 11/2007 |
| WO | 2016071151 A1 | 5/2016 |

OTHER PUBLICATIONS

International Search Report from corresponding PCT/US2017/037855 dated Nov. 2, 2017.

* cited by examiner

*Primary Examiner* — Mark V Stevens
(74) *Attorney, Agent, or Firm* — Caesar Rivise, PC

(57) ABSTRACT

Disclosed are: (a) controlled release matrix particles containing 10-70 wt. % of a hydrophobic active ingredient, 21-72 wt. % of a polysaccharide, 3.80-12 wt. % of a crosslinking agent, 1.00-6 wt. % of a catalyst and 0.10-5 wt. % of a silica flow aid; (b) controlled release core/shell particles containing 10-70 wt. % of a hydrophobic active ingredient, 1.0-3.2 wt. % of an epoxidized oil, 21-64 wt. % of a polysaccharide, 7.6-23% of an amine-functionality containing material, and 0.10-5 wt. % of a silica flow aid; and (c) hybrid particles wherein the core/shell particles are contained in a matrix. Also disclosed are methods for making the particles and compositions containing the particles.

21 Claims, 8 Drawing Sheets

100

POLYSACCHARIDE DELIVERY PARTICLE

CROSS REFERENCE TO RELATED APPLICATIONS

Figure 1A:

This application claims the benefit of U.S. Provisional Patent Application No. 62/351,597, filed Jun. 17, 2016, the contents of which application are incorporated herein by reference in their entirety for all purposes.

BACKGROUND OF THE INVENTION

1. Field of Invention

This invention relates to controlled release compositions, encapsulation compositions and methods for making and using them.

2. Description of Related Art

There are many microencapsulated delivery systems disclosed in the art to control the release of the encapsulated active, or provide release when a specific trigger is applied. Such systems have previously suffered from a number of drawbacks.

Core/shell microcapsules that provide release of active upon application of shear or friction are generally not environmentally biodegradable. Such capsules are made using reactive monomers that are not Generally Regarded As Safe (GRAS), and are generally unsafe for direct contact with skin or mucosa membranes. Such microcapsules are made via chemical processes that generally require long batch cycle times.

Polymers that are used to develop a membrane around the active material need to be crosslinked to provide a sufficient barrier to retain the encapsulated active until its desired release. The crosslinking increases the lifetime of these polymers in the environment because the functional groups that breakdown the polymer via microbes are the same functional groups that are used to produce a crosslinked material.

Biodegradable polymers, such as polysaccharides, are utilized to encapsulate volatile actives. However, these systems prematurely release the encapsulated active, especially in any formulation that contains water.

When polysaccharide-based microcapsules are incorporated into anhydrous product forms, these materials will release the active as soon as they come in contact with water, or prematurely release the encapsulated payload in the supply chain due to humidity/temperature effects. Often, it is desired to retain the active even after exposure to water. For example, it is desired to have a microcapsule survive the dilute environment in a washing machine, deposit onto the laundered fabrics, retain fragrance within the microcapsule during high temperature drying, and subsequently release the fragrance over a long duration of time from the fabric. It may be desired to have bursts of fragrance from an antiperspirant or deodorant product even in the absence of perspiration. It may be desired to retain flavor during the baking process, and release the flavor when the baked item is chewed. It may be desired to incorporate flavor particles directly into the dough when making snack foods (such as potato chips), rather than sprinkling on the flavors after the chip is fried. Such an approach can eliminate the mess associated with consuming flavored chips. It may be desired to incorporate flavor particles into a chewing gum to deliver a burst of a flavor upon chewing.

In order to deliver a consumer noticeable benefit, yet deliver that benefit at a low cost, encapsulation is used to isolate a uniquely different fragrance or flavor active from the non-encapsulated fragrance or flavor that is incorporated into the formulation. Acclamation to a flavor or fragrance requires a much higher concentration of the same fragrance or flavor to achieve noticeability. The invention allows one to encapsulate a uniquely different fragrance or flavor to incorporate into the composition, and achieve noticeability at significantly lower concentrations of the encapsulated active.

Friable capsules that are disclosed in the art are specifically core/shell capsules. "Matrix" type of morphology wherein small droplets of the active material are surrounded by shell material are exclusively found in the area of water triggered release technologies (flavors, fragrances, vitamins, silicone oils, etc.). Matrix particles are generally not designed to provide friction-triggered release.

In order to incorporate friable microcapsules into anhydrous products (for example antiperspirant/deodorants, dry laundry powder, baking goods), it is necessary to remove the water from slurries of core/shell microcapsule. Spray drying is a well-known, commercially viable, and inexpensive way to achieve a dry powder. Spray drying of water insoluble, friable microcapsules must be done with utmost care to minimize fracture of the microcapsules during the spray drying process. Generally, only small particle size particles can be dried effectively without fracturing. The high fracture strength of these small particles reduces the performance benefit (i.e. normal consumer activities would not generate enough friction or stress to fracture a sufficient number of these microcapsules). Larger dry particles are preferred since they are easier to fracture, and they can deliver a greater volume of encapsulated material when fractured. However, such large core/shell particles will fracture during the spray drying process.

Hence, it is difficult to achieve a free flowing powder, water insoluble or water swellable, environmentally biodegradable, matrix microcapsule particle that provides a non-water triggered release profile. It is even more difficult to achieve an affordable microcapsule in a dehydrated powder form without incurring significant loss of the encapsulated active during the dehydration process. It is even more difficult to achieve a microcapsule that retains the encapsulated actives even under highly dilute aqueous conditions.

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

A first aspect of the invention comprises controlled release particles.

In certain embodiments, the controlled release particles comprise 10-70 wt. % of a hydrophobic active ingredient, 21-72 wt. % of a polysaccharide, 3.80-12 wt. % of a crosslinking agent, 1.00-6 wt. % of a catalyst, 0.10-5 wt. % of a silica flow aid, and optionally 0.10-5 wt. % of a desiccant, wherein the controlled release particles are anhydrous and the hydrophobic active ingredient is encapsulated in a crosslinked polysaccharide matrix effective to retain the hydrophobic active ingredient upon exposure to weater and effective to release the hydrophobic active ingredient in response to friction.

In certain embodiments, the controlled release particles further comprise 1.05-3.30 wt. % of an epoxidized oil and 1.00-23 wt. % of an amine-functionality containing material selected from the group consisting of poly(diallyl dimethylammonium) halides, copolymers of poly(diallyl dimethylammonium) chloride and polyvinyl pyrrolidone, acrylamides, imidazoles, imidazolinium halides, polyvinyl amine, copolymers of polyvinyl amine and N-vinyl formamide, polyvinylformamide, copolymers of polyvinylamine and polvyinylalcohol oligimers of amines, diethylenetriamine, ethylene diamine, bis(3-aminopropyl)piperazine, N,N-bis-(3-aminopropyl)methylamine, tris(2-aminoethyl)amine, polyethyleneimime, derivatized polyethyleneimine, ethoxylated polyethyleneimine, polybutadiene/styrene, polybutadiene/acrylonitrile, carboxyl-terminated polybutadiene/acrylonitrile, chitosan with various degrees of deacetylation, carboxymethyl chitosans, glycol chitosans, whey protein, sodium caseinate, silk protein, polyamines and mixtures thereof.

In certain other embodiments, the controlled release particle comprises 10-70 wt. % of a hydrophobic active ingredient, 1.0-3.2 wt. % of an epoxidized oil, 21-64 wt. % of a polysaccharide, 7.6-23% of an amine-functionality containing material, and 0.10-5 wt. % of a silica flow aid, wherein the controlled release particles are anhydrous and the hydrophobic active ingredient is in a core encapsulated by a shell effective to retain the hydrophobic active ingredient upon exposure to water and effective to release the hydrophobic active ingredient in response to friction.

In certain embodiments, the hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

In certain embodiments, the hydrophobic ingredient is a mixture of a hydrophobic active ingredient and a diluent. The diluent is used to change the properties of the hydrophobic material, for example, the polarity, the melting point, the surface tension, the viscosity, the density, or the volatility of the hydrophobic active. In certain embodiments, the diluent is a member selected from plant waxes, animal waxes, petroleum based waxes, synthetic waxes, mineral waxes, brominated oils, hydrophobically modified inorganic particles, nonionic emulsifiers, oil thickening agents.

In certain embodiments, the polysaccharide is a member selected from the group consisting of octenyl succinic acid anhydride modified starch, gum arabic, xanthan gum, gellan gum, pectin gum, konjac gum and carboxyalkyl cellulose.

In certain embodiments, the crosslinking agent is a member selected from the group consisting of dimethyldihydroxy urea, dimethyloldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(acrylic acid), poly(methacrylic acid), poly(maleic acid), poly(methylvinylether-co-maleate) copolymer, copolymers of acrylic acid and copolymers of maleic acid.

In certain embodiments, the catalyst is a member selected from the group consisting of ammonium chloride, ammonium sulfate, aluminum chloride, magnesium chloride, magnesium nitrate and sodium hypophosphite.

In certain embodiments, the silica flow aid is a member selected from the group consisting of fumed silica, precipitated silica, calcium silicate, aluminosilicate, and combinations thereof.

Preferably, the epoxidized oil is epoxidized soybean oil or other epoxidized vegetable oils. Epoxy oils can be epoxy resins. Epoxy resins refer to molecular species comprising two or more epoxide groups per molecule. Epoxy resins can contain mono-epoxides as reactive diluents, but the main constituents by weight of such resins are still di and/or higher functionality species (containing two or more epoxide groups per molecule). Precursor epoxy resins include but are not limited to diglycidyl ether of bisphenol-A, diglycidyl ethers of bisphenol-A alkoxylates, epoxy novolac resins, expoxidized soy oil, epoxidized linseed oil, epoxidized vegetable oils, epichlorohydrin, a glycidyl ether type epoxy resin derived from a polyphenol by reaction with epichlorohydrin, and combinations thereof. In another embodiment, precursor epoxy resins are modified by combining them with the polypeptide compositions.

In certain embodiments, the controlled release particles have a diameter from 0.1 microns to less than 100 microns.

In certain embodiments, the controlled release particles have an Environmental Degradability index greater than 80.

In certain embodiments, the amine-functionality containing material is a member selected from the group consisting of poly(diallyl dimethylammonium) halides, copolymers of poly(diallyl dimethylammonium) chloride and polyvinyl pyrrolidone, acrylamides, imidazoles, imidazolinium halides, polyvinyl amine, copolymers of polyvinyl amine and N-vinyl formamide, polyvinylformamide, copolymers of polyvinylamine and polvyinylalcohol oligimers of amines, diethylenetriamine, ethylene diamine, bis(3-aminopropyl)piperazine, N,N-bis-(3-aminopropyl)methylamine, tris(2-aminoethyl)amine, polyethyleneimime, derivatized polyethyleneimine, ethoxylated polyethyleneimine, polybutadiene/styrene, polybutadiene/acrylonitrile, carboxyl-terminated polybutadiene/acrylonitrile, chitosan with various degrees of deacetylation, carboxymethyl chitosans, glycol chitosans, whey protein, sodium caseinate, silk protein, polyamines and mixtures thereof.

In certain embodiments, the desiccant is a member selected from the group consisting of calcium sulfate, sodium sulfate, calcium silicate, hydrophilic aluminosilicates, magnesium sulfate, silica gel, crosslinked polyacrylates and combinations thereof.

A second aspect of the invention comprises a method for preparing the controlled release particles of the invention.

In certain embodiments, the method comprises: mixing the hydrophobic active ingredient with the polysaccharide and water to provide an emulsion; agitating the emulsion to provide a modified emulsion containing hydrophobic active ingredient droplets with a volume average diameter of less than 5 microns; mixing with the modified emulsion the crosslinking agent and the catalyst to provide a spray-ready emulsion; spray drying the spray-ready emulsion to provide a powder; adding the silica flow aid to the powder to provide a modified powder; optionally adding a desiccant; heating the modified powder to form the controlled release particles; and optionally removing the desiccant via sieving.

In certain embodiments, the method comprises: mixing the hydrophobic active ingredient with the epoxidized oil to provide a homogeneous solution; mixing the homogeneous solution with a polysaccharide solution comprising the polysaccharide, the crosslinking agent, the catalyst and water to provide an emulsion; agitating the emulsion to provide a modified emulsion containing hydrophobic active ingredient droplets with a volume average diameter of less than 5 microns; mixing with the modified emulsion the amine-functionality containing material to provide a spray-ready emulsion; spray drying the spray-ready emulsion to provide a powder; adding silica flow aid to the powder to provide a modified powder; and heating the modified powder to form the controlled release particles.

In certain embodiments, the method comprises: mixing the hydrophobic active ingredient with the epoxidized oil to provide a homogeneous solution; mixing the homogeneous solution with a polysaccharide solution comprising the polysaccharide and water to provide an emulsion; agitating the emulsion to provide a modified emulsion containing hydrophobic active ingredient droplets with a volume average diameter of less than 20 microns; mixing with the modified emulsion the amine-functionality containing material to provide a spray-ready emulsion; spray drying the spray-ready emulsion to provide a powder; and adding silica flow aid to the powder, with optional heating, to provide the controlled release particles.

In certain embodiments, the modified powder is heated within a temperature range of 130-185° C.

In certain embodiments, the heating of the powder is achieved by using convective, conductive, or radiative heat transfer.

A third aspect of the invention comprises a composition comprising the controlled release particles of the invention, wherein the composition is a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye and a unit dose detergent comprising a detergent and the controlled release particles in a water soluble film.

In certain embodiments, the composition further comprises at least one suspension agent to suspend the controlled release particles, wherein the at least one suspension agent is at least one member selected from the group consisting of a rheology modifier, a structurant and a thickener.

In certain embodiments of the composition, the at least one suspension agent has a high shear viscosity at, 20 $sec^{-1}$ shear rate and at 21° C., of from 1 to 7000 cps and a low shear viscosity, at 0.5 $sec^{-1}$ shear rate at 21° C., of greater than 1000 cps.

In certain embodiments, the composition has a high shear viscosity, at 20 $sec^{-1}$ and at 21° C., of from 50 to 3000 cps and a low shear viscosity, at 0.5 $sec^{-1}$ shear rate at 21° C., of greater than 1000 cps.

In certain embodiments of the composition, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

In certain embodiments, the composition has at least two controlled release technologies, which release different hydrophobic oil compositions and are selected from the group consisting of neat oils, friction-triggered release microcapsules and water-triggered release microcapsules.

BRIEF DESCRIPTION OF SEVERAL VIEWS OF THE DRAWINGS

The invention will be described in conjunction with the following drawings, wherein:

FIG. 1A is a photograph of the fabrics of Examples 4A (left) and 4I (right).

FIG. 1B is an SEM image of the microcapsules used to prepare fabrics of Example 4A.

FIG. 1C is an SEM image of the microcapsules used to prepare fabrics of Example 4I .

FIG. 2A is an SEM image of the microcapsules used to prepare fabrics of Example 5G.

FIG. 2B is an SEM image of the microcapsules used to prepare fabrics of Example 5H.

FIG. 3 is a graph of weight and derivative weight against temperature, wherein the solid lines represent Example 5G and the dashed lines represent Example 5H.

FIG. 4 shows a DSC Thermogram of powder with (Example 5H) and without (Example 5G) added fumed silica.

FIG. 5 is a graph of weight against temperature.

FIGS. 6A and 6B are optical microscopy images.

FIGS. 7A, 7B and 7C are SEM images of the fabric of Example 11A at 210×, 820× and 1950× magnification, respectively.

FIGS. 8A, 8B, 8C and 8D are SEM images of the fabric of Example 11B at 255×, 960×, 1500× and 950× magnification, respectively.

FIGS. 9A, 9B, 9C and 9D are SEM images of the fabric of Example 11C at 860×, 4000×, 910× and 2100× magnification, respectively.

FIGS. 10A, 10B and 10C are SEM images of the fabric of Example 11D at 260×, 4800× and 910× magnification, respectively.

FIGS. 11, 12 and 13 are volatile loss graphs of % mass against temperature.

DETAILED DESCRIPTION OF PREFERRED EMBODIMENTS OF THE INVENTION

Glossary

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term “about” is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, “alkyl” whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

Particles

The invention addresses one or more of the prior art deficiencies described above by providing controlled release particles. The particles are particularly well-suited for use in encapsulation of hydrophobic, nonpolar materials. The controlled release particles are preferably anhydrous sufficiently friable to release the hydrophobic active ingredient in response to friction. The particles can be subdivided into three different embodiments: (1) matrix particles; (2) core/shell particles; and (3) hybrid particles comprise a matrix containing core/shell particles.

The matrix particles preferably comprise 10-70 wt. % of a hydrophobic active ingredient, 21-72 wt. % of a polysaccharide, 3.80-12 wt. % of a crosslinking agent, 1.00-6 wt. % of a catalyst and 0.10-5 wt. % of a silica flow aid, wherein all percentages by weight of particle ingredients specified herein are based on a total weight of the particles, unless otherwise specified. The hydrophobic active ingredient is encapsulated in a crosslinked polysaccharide matrix effective to retain the hydrophobic active ingredient upon exposure to water and effective to release the hydrophobic active ingredient in response to friction.

The core/shell particles preferably comprise 10-70 wt. % of a hydrophobic active ingredient, 1.0-3.2 wt. % of an epoxidized oil, 21-64 wt. % of a polysaccharide, 7.6-23% of an amine-functionality containing material, and 0.10-5 wt. % of a silica flow aid, wherein the hydrophobic active ingredient is in a core encapsulated by a shell effective to retain the hydrophobic active ingredient upon exposure to water and effective to release the hydrophobic active ingredient in response to friction.

The hybrid particles preferably comprise 10-70 wt. % of a hydrophobic active ingredient, 21-72 wt. % of a polysaccharide, 3.80-12 wt. % of a crosslinking agent, 1.00-6 wt. % of a catalyst, 0.10-5 wt. % of a silica flow aid, 1.05-3.30 wt. % of an epoxidized oil and 1.00-23 wt. % of an amine-functionality containing material.

The hydrophobic active ingredient is a hydrophobic substance that is active (or effective) to provide a desired effect, alone or in combination with other substances and/or conditions. It is present in the particles in an amount effective to provide a desired effect. The amount can be, e.g., from 1 wt. % or 5 wt. % or 10 wt. % to 25 wt. % or 50 wt. % or 70 wt. % or 80 wt. %.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an LogP (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol and derivatives of bis(p-dimethylaminophenyl)methylamine, for example N[bis(p-dimethylaminophenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like Suitable pigments include but are not limited to pearl pigments of mica group such as titanium dioxide-coated mica and colored titanium dioxide-coated mica; and pearl pigments of bismuth oxychlorides such as colored bismuth oxychloride. Such pigments are available on the market under various trade names: Flamenco series (by the Mearl Corporation), TIMIRON COLORS (by MERCK) as titanium dioxide-coated mica, Timica Luster Pigments (by MEARL). Cloisonee series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Fungicidal compounds which in the present invention include isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4, 5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethylisothiazolinone, 4,5-Dichloro-2-n-octyl-3(2H)-isothiazolone and 1,2-benzisothiazolin-3-one.

Suitable herbicides include but are not limited to 2-(2-chloro-4-methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins. Preferably, the polyolefins are crosslinked such that they are form stable upon heating above their crystalline melting point. Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying resin materials include unsaturated natural resins such as rosin or derivatives thereof, such as rosin esters of polyols such as glycerol or pentaerythritol, hydrogenated rosins or dehydrogenerated rosins Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil. Suitable vegetable oils include but are not limited to oils derived from palm, corn, canola, sunflower, safflower, rapeseed, castor, olivek, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorilonite or kaolin, hydrophobically modified clays, hydrophobically modified precipitated silicas or fumed silicas. Examples of materials that can alter the surface tension of the active phase in the particle are nonionic emulsifiers such as polysorbate-type nonionic surfactant (e.g. Tween™), alcohol ethoyxlate based surfactants (e.g. Genapol™). Examples of oil thickening agents are waxes mentioned above, modified organopolysiloxanes, silicone gums, hydrogenated castor oil, paraffin oils, polyolefins, and the like.

The polysaccharide is present in the particles in an amount effective to provide a coating and/or matrix having the desired structural properties. The amount can be, e.g., from 5 wt. % or 10 wt. % or 21 wt. % or 25 wt. % to 50 wt. % or 64 wt. % or 72 wt. % or 80 wt. %.

Polysaccharides having emulsifying and emulsion stabilizing capacity are preferred. The polysaccharide is preferably a member selected from the group consisting of octenyl succinic acid anhydride modified starch, gum arabic, xanthan gum, gellan gum, pectin gum, konjac gum and carboxyalkyl cellulose.

The crosslinking agent is present in the matrix and hybrid particles of the invention in an amount effective (in the presence of the catalyst) to crosslink the polysaccharide to an extent effective to provide the particles with desired durability. The amount can be, e.g., from 1 wt. % or 2 wt. % or 3.80 wt. % or 5 wt. % to 8 wt. % or 10 wt. % or 12 wt. % or 15 wt. %.

The crosslinking agent is preferably a member selected from the group consisting of dimethyldihydroxy urea, dimethyloldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(acrylic acid), poly(methacrylic acid), poly(maleic acid), poly(methylvinylether-co-maleate) copolymer, copolymers of acrylic acid and copolymers of maleic acid.

The catalyst is present in the matrix and hybrid particles of the invention in an amount effective to catalyze the crosslinking of the polysaccharide to an extent effective to provide the particles with desired durability. The amount can be, e.g., from 0.1 wt. % or 0.5 wt. % or 1 wt. % or 2 wt. % to 2.5 wt. % or 5 wt. % or 6 wt. % or 7 wt. %.

The catalyst is preferably a reducing agent and/or electron donor, and is more preferably a member selected from the group consisting of ammonium chloride, ammonium sulfate, aluminum chloride, magnesium chloride, magnesium nitrate and sodium hypophosphite.

The silica flow aid is present in the particles in an amount effective to minimize or eliminate clumping and the presence of flakes in the particles. The amount can be, e.g., from 0.05 wt. % or 0.10 wt. % or 0.5 wt. % or 1 wt. % to 2.5 wt. % or 5 wt. % or 7.5 wt. % or 10 wt. %.

The silica flow aid is preferably a precipitated silica and more preferably a fumed silica. Hydrophobic silicas are preferred. Silicas that have a surface area greater than 60 $m^2/g$ are more preferred. Preferred fumed silicas include AEROSIL R 812. Preferred precipitated silicas include SYLOID 244, which is hydrophobic and ZEOTHIX, which is hydrophilic. Alternatively, the silica flow aid comprises calcium silicate, such as Hubersorb 250 or 600 grades sold by Huber Corporation. Alternatively, the silica flow aid is an aluminosilicate such as the Zeolex grades sold by Huber Corporation.

Optionally a desiccant is added to the powder to absorb the moisture that is released from the particle during heating, such that the moisture does not act to plasticize the particle and form large aggregates. Suitable desiccants include but are not limited to calcium sulfate, sodium sulfate, calcium silicate, hydrophilic aluminosilicates, magnesium sulfate, silica gel, crosslinked polyacrylates, and the like. It is desirable to have the desiccant particle size at least 5 times the median particle size of the powder being heated, such that after the powder heating process, the desiccants can be removed via sieving. The amount can be, e.g., from 0.05 wt. % or 0.10 wt. % or 0.5 wt. % or 1 wt. % to 2.5 wt. % or 5 wt. % or 7.5 wt. % or 10 wt. %.

The epoxidized oil is present in the core/shell and hybrid particles in an amount from 0.1 wt. % or 0.5 wt. % or 1.05 wt. % or 2 wt. % to 2.5 wt. % or 3 wt. % or 3.3 wt. % or 5 wt. %.

The epoxidized oil is preferably epoxidized soybean oil.

The amine-functionality containing material is present in the core/shell and hybrid particles in an amount from 2.5 wt. % or 5 wt. % or 7.6 wt. % or 10 wt. % to 12 wt. % or 15 wt. % or 23 wt. % or 30 wt. %.

The amine-functionality containing material is preferably a member selected from the group consisting of poly(diallyl dimethylammonium) halides, copolymers of poly(diallyl dimethylammonium) chloride and polyvinyl pyrrolidone, acrylamides, imidazoles, imidazolinium halides, polyvinyl amine, copolymers of polyvinyl amine and N-vinyl formamide, polyvinylformamide, copolymers of polyvinylamine and polvyinylalcohol oligimers of amines, diethylenetriamine, ethylene diamine, bis(3-aminopropyl)piperazine, N,N-bis-(3-aminopropyl)methylamine, tris(2-aminoethyl) amine, polyethyleneimime, derivatized polyethyleneimine, ethoxylated polyethyleneimine, polybutadiene/styrene, polybutadiene/acrylonitrile, carboxyl-terminated polybutadiene/acrylonitrile, chitosan with various degrees of deacetylation, carboxymethyl chitosans, glycol chitosans, whey protein, sodium caseinate, silk protein, polyamines and mixtures thereof.

The controlled release particles are preferably spherical but non-spherical shapes are also within the scope of the invention. The particles preferably have a diameter from 0.05-250 microns, or from 0.1 microns to less than 100 microns.

In certain embodiments, the controlled release particles have an Environmental Degradability index greater than 25 or greater than 75 or greater than 80.

Method of Making the Particles

The matrix particles of the invention are provided by a method comprising: mixing the hydrophobic active ingredient with the polysaccharide and water to provide an emulsion; agitating the emulsion to provide a modified emulsion containing hydrophobic active ingredient droplets with a volume average diameter of less than 5 microns; mixing with the modified emulsion the crosslinking agent and the catalyst to provide a spray-ready emulsion; spray drying the spray-ready emulsion to provide a powder; adding the silica flow aid to the powder to provide a modified powder; and heating the modified powder to form the controlled release particles.

The hybrid particles of the invention are provided by a method comprising: mixing the hydrophobic active ingredient with the epoxidized oil to provide a homogeneous solution; mixing the homogeneous solution with a polysaccharide solution comprising the polysaccharide, the crosslinking agent, the catalyst and water to provide an emulsion; agitating the emulsion to provide a modified emulsion containing hydrophobic active ingredient droplets with a volume average diameter of less than 5 microns; mixing with the modified emulsion the amine-functionality containing material to provide a spray-ready emulsion; spray drying the spray-ready emulsion to provide a powder; adding silica flow aid to the powder to provide a modified powder; and heating the modified powder to form the controlled release particles.

The core/shell particles of the invention are provided by a method comprising: mixing the hydrophobic active ingredient with the epoxidized oil to provide a homogeneous solution; mixing the homogeneous solution with a polysaccharide solution comprising the polysaccharide and water to provide an emulsion; agitating the emulsion to provide a modified emulsion containing hydrophobic active ingredient droplets with a volume average diameter of less than 20 microns; mixing with the modified emulsion the amine-functionality containing material provide a spray-ready emulsion; spray drying the spray-ready emulsion to provide a powder; adding silica flow aid to the powder to provide a modified powder; and heating the modified powder to form the controlled release particles.

In the case of the matrix and hybrid particle method, the incorporation of crosslinking agent, catalyst and polysaccharide into an emulsion achieves a homogeneous concentration of these materials in the final spray dried powder. Dry mixing the crosslinking agent and catalyst after the polysaccharide emulsion is dried does not lead to the desired result as shown in the Examples below.

The emulsion is agitated to provide oil droplets in the emulsion which are preferably 0.5 to 10 microns, and more preferably 1 to 5 microns in volume average diameter.

In the matrix, core/shell and hybrid methods, spray drying of the emulsion is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

The silica flow aid is added to the dry powder to improve the flowability of the powder. Addition of the silica flow aid minimizes the agglomeration of particles during the curing process, and surprisingly reduces the volatility of the encapsulated active. The exact mechanism of interactions is not understood; however, thermal analysis clearly shows a desired reduction in volatility of the encapsulated active.

Without the addition of silica, the powder would agglomerate during the curing process. To achieve a particle size less than 100 microns, it would be necessary to grind the agglomerated powder, which would be detrimental to the particles, because it could lead to fracture of the particles and premature release of the encapsulated active material.

The powder is then heated to achieve the desired interaction between polysaccharide, crosslinking agent and the catalyst and provide a matrix particle that can provide friction-triggered release of the encapsulated active.

The modified powder is preferably heated with a temperature range of 130-185° C. for a preferred curing time within the range of 3-60 minutes, more preferably 5-30 minutes. Insufficient curing may occur at temperatures below 130° C. and/or for lesser curing times. In order to minimize the degradation of the matrix components, minimize premature fracture of the particle, and minimize volatile loss of encapsulated active materials, the maximum curing temperature should not exceed 185° C. Curing conditions can be adjusted to achieve a desired reduction in particle solubility in water, and desired release profile of the encapsulated active.

Curing of the particles can be achieved by any suitable heating means. There are three primary methods of heat transfer: convective, conductive, and radiative. Convective heat transfer uses air to fluidize the particles, and the temperature of the air is manipulated to achieve the desired heating. Conductive heat transfer utilizes either electric heating in a kiln, or oil heating in a jacketed paddle mixer (auger mixer, cement mixer, ribbon blender, U-trough mixer, and the like). The powder is rotated in the mixer and heating occurs by transfer of heat from the metal surface of the mixer to the powder touching that surface. Radiative heat transfer utilizes infrared waves, radio frequency waves, microwaves to achieve the desired heating. Any of these methods can be used to achieve the desired heat treatment of the particle. Suitable heating means include but are not limited to one or more of the following: oven, rotary infrared dryers, microwave radiative dryers, radio frequency radiative dryers, kiln or calciner, steam tube dryers, tray dryers, fluid bed dryers, granulators, baking ovens, serpentine ovens, jacketed auger mixers, jacketed ribbon blenders, and the like.

Gentle agitation is preferably provided during curing to minimize fracture of the particles.

Matrix design of the particles results in more robust particles—even if there is some fracture of particles, only that portion of the particle releases the oil, the remaining two halves of particles can be fractured further to release the active material. This is a significant advantage vs. core/shell capsules wherein fracture of the particle results in total loss of the encapsulated oil.

Advantages of at least some embodiments of the inventive method include:

a) One-pot process: two additional ingredients are added during flavor or fragrance oil encapsulation process utilizing polysaccharides;

b) Materials used are GRAS, environmental fate of these materials meets environmental biodegradability criteria;

c) Can be used in a variety of applications: foods, flavors, nutraceuticals, pharmaceuticals, household care, personal care, beauty care;

d) Utilizes a commercially available, relatively inexpensive spray drying technique to engineer the particle;

e) Yields a water insoluble, anhydrous particle that can encapsulate lipophilic actives with reduced volatile loss at elevated temperatures;

f) Is not a core/shell particle (releases the total encapsulated active upon application of the release trigger), but a matrix morphology wherein a portion of the encapsulated active is released upon a release trigger; and g) offers multiple release triggers to empty the encapsulated active from the controlled release particle (e.g., friction, enzyme).

Compositions Containing the Particles

The invention further comprises compositions comprising the controlled release particles. Such compositions include but are not limited to a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye, and a unit dose detergent comprising a detergent and the controlled release particles in a water soluble film.

The fluid compositions preferably further comprise at least one suspension agent to suspend the controlled release particles, wherein the at least one suspension agent is at least one member selected from the group consisting of a rheology modifier, a structurant and a thickener. The at least one suspension agent preferably has a high shear viscosity at, 20 $sec^{-1}$ shear rate and at 21° C., of from 1 to 7000 cps and a low shear viscosity, at 0.5 $sec^{-1}$ shear rate and at 21° C., of greater than 1000 cps or 1000-200,000 cps. In certain embodiments, the composition has a high shear viscosity, at 20 sec$^{-1}$ and at 21° C., of from 50 to 3000 cps and a low shear viscosity, at 0.5 sec$^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

In certain embodiments, the composition has at least two controlled release technologies, which release different hydrophobic oil compositions and are selected from the group consisting of neat oils, friction-triggered release microcapsules and water-triggered release microcapsules.

When hybrid particles are incorporated into an aqueous solution, with or without detergent actives, the water plasticizes the powders to yield swollen particle, or particle aggregates. Such swollen or particle aggregates have a higher probability of getting entrapped in fabrics during a laundering cycle. Particle swelling in combination with incorporation of amine containing materials in the particle has the desired effect of increasing the viscoelasticity of the particle and the cationic charge of the particle. Cationic particles have a higher probability of adhering to anionic fabric in the laundering environment. Amine-functionality containing materials that can be incorporated into the spray-ready emulsion, which may have a favorable effect on adhesion of particles onto skin, hair, or fabric substrates comprise a polymer selected from the group consisting of polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, copolymers of polyvinylamine and polvyinylalcohol oligimers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimime, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; chitosan with various degrees of deacetylation, carboxymethyl chitosans, glycol chitosans; proteinaceous materials with various molecular weights, including whey protein, sodium caseinate, silk protein; polyamines and mixtures thereof.

The invention will be illustrated in more detail with reference to the following Examples, but it should be understood that the present invention is not deemed to be limited thereto.

EXAMPLES

Materials and Methods

The following perfume oil composition is used throughout the Examples.

| CAS | Name | Octanol/water Partition Coefficient (logP) | Boiling Point, ° C. | wt % |
|---|---|---|---|---|
| 67634-00-8 | Allyl_amyl_glycolate | 2.81 | 231 | 6.10% |
| 7493-57-4 | (−)-Citronellol | 2.76 | 279 | 5.11% |
| 150-84-5 | Citronellyl_acetate | 3.7 | 222 | 6.49% |
| 103-95-7 | Cyclamen_aldehyde (cymal) | 3.62 | 290 | 6.23% |
| 18592-13-7 | Dihydromyrcenol | 3.08 | 195 | 5.11% |
| 68647-72-3 | d-Limonene | 4.38 | 176 | 4.46% |
| 7452-79-1 | Ethyl_2-methylbutyrate | 1.91 | 133 | 4.26% |
| 121-32-4 | Ethyl_vanillin | 1.53 | 294 | 5.44% |
| 125109-85-5 | Florhydral | 3.59 | 295 | 6.23% |
| 142-92-7 | Hexyl_acetate | 2.64 | 165 | 4.72% |
| 14901-07-6 | beta-Ionone | 4.02 | 267 | 6.29% |
| 97-54-1 | Isoeugenol | 1.85 | 264 | 5.37% |
| 2437-25-4 | Lauronitrile | 4.84 | 251 | 5.93% |
| 78-70-6 | Linalool | 2.44 | 204 | 5.05% |
| 6008-27-1 | Nonalactone | 1.3 | 201 | 5.11% |
| 88-41-5 | o-tert-Butylcyclohexyl_acetate (verdox) | 3.87 | 223 | 6.49% |
| 177772-08-6 | Undecavertol | 3.06 | 242 | 5.57% |
| 87731-18-8 | Violiff | 2.11 | 214 | 6.03% |

Thermal Gravimetric Analysis

A Thermal Gravimetric Analysis pan is exposed to a Bunsen burner to remove any residue from the pan. Approximately 5 milligrams of sample is weighed onto a pan of a Thermal Gravimetric Analyzer (Model TGA Q500). Next the sample is exposed to a temperature ramp that comprises from an initial temperature of 25 degrees Celsius, a heating ramp of 10 Celsius degrees per minute, to a final temperature of 600 degrees Celsius. A graph of sample mass loss versus temperature is plotted to gain insights into transitions—water evaporation, volatile active evaporation, degradation of the microcapsule materials.

Differential Scanning Calorimetry

Approximately 5 milligrams of sample is weighed onto a pan of a Differential Scanning Calorimeter (Model DSC Q2000) and hermetically sealed. The sample pan is then exposed to a temperature ramp that comprises from an initial temperature of 25 degrees Celsius, a heating ramp of 10 Celsius degrees per minute, to a final temperature of 250 degrees Celsius, and then a temperature decrease ramp of negative 10 Celsius degrees per minute, to a final temperature of 25 degrees Celsius. A graph of heat flow versus temperature provides insights into thermal transitions that occur in the powder.

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Detergent/Water Dissolution+Fabric Preparation

To 9.75 grams of a detergent solution (1 gram of powder detergent added to 99 grams of water, then filtered through Whatman 597 filter catalog number 10311808) is added powder or slurry that achieves a concentration of approximately 1 wt % perfume oil in the detergent solution. For water solubility, the powder is simply dosed into water rather than detergent solution. The solution is mixed at 200 rpm with a stir bar, for 1 hour at 20 C to simulate a cold water laundry cycle, or 33.3 C to simulate a warm water laundry cycle. For detergent dissolution, the sample is mixed at 200 RPM for 30 minutes at 33.3 degrees Celsius. A pre-weighed 3 inch diameter circle of black 100% cotton fabric is placed in a Buchner funnel attached to a vacuum line. 2 mL of the solution is then poured through the fabric, followed by a wash of 2 mL water. The fabric is allowed to air dry overnight.

Odor Evaluation

There are 2 techniques utilized to evaluate odor of fabrics:

1) The dried fabrics from the Detergent/Water Dissolution+Fabric Preparation test is evaluated olfactively by a panel before and after rubbing.

The dried fabrics from the Detergent/Water Dissolution+Fabric Preparation test is evaluated by an Odor Meter (Shinyei Technology model OMX-SRM) before and after rubbing Biodegradability Biodegradability testing is carried out according to protocol OECD 301D. 5 mg/L material is placed into BOD bottles in water collected from the Lehigh River (Bethlehem, Pa). The bottles are checked for dissolved oxygen at 0, 7, 14, and 28 days. Intermittent points can also be taken since an asymptotic value may be reached much sooner than 28 days. The percent degradation is analyzed against the positive control starch. See Example 24 for a detailed description of the analysis and calculations of Biodegradability Index.

Example 1

Starch Encapsulated Perfume 88.75 g of HICAP 100 modified starch (Ingredion) is added to 266.25 g of water at 24° C. to make approximately a 25% wt. % solution.

The mixture is agitated at 600 RPM using a RW20 digital mixer with a turbine, 4-pitched blade impeller 2 inches in diameter, for 20 minutes.

88.75 g perfume oil is added near the vortex of the starch solution.

The emulsion is homogenized at 20,000 RPM for 3 minutes using a Unidrive X1000 homogenizer with a rotor-stator shaft.

Upon achieving a perfume droplet median volume average diameter of less than 5 microns, the emulsion is pumped to a spray drying tower and atomized using a centrifugal atomizer with co-current airflow for drying. The inlet air temperature is set at 185-205° C., the exit air temperature is stabilized at 85-103° C.

Dried particles of the starch encapsulated perfume oil are collected from the cyclone.

Example 2A

Starch Encapsulated Perfume with Acid and Catalyst (Comparative Example)

To 88.75 grams of powder from Example 1 is added 7.5 grams of citric acid, and 3.75 grams of sodium hypophosphite monohydrate, and dry mixed by agitation of the jar.

Example 2B

Starch Encapsulated Perfume with Acid and Catalyst 88.75 g of HICAP 100 modified starch (Ingredion) is added to 266.25 g of water at 24° C. to make approximately a 25% wt. % solution.

The mixture is agitated at 600 RPM using a RW20 digital mixer with a turbine, 4-pitched blade impeller 2 inches in diameter, for 20 minutes.

88.75 g perfume oil is added near the vortex of the starch solution.

The emulsion formed is agitated for an additional 20 minutes (at 600 RPM).

Upon achieving a perfume droplet median volume average diameter of less than 5 microns, 15 grams of citric acid, and 7.5 grams of sodium hypophosphite monohydrate (Aldrich) are added to the emulsion. After mixing for 5 minutes, the emulsion is pumped to a spray drying tower and atomized using a centrifugal atomizer with co-current airflow for drying. The inlet air temperature is set at 205-210° C., the exit air temperature is stabilized at 98-103° C.

Dried particles of the starch encapsulated perfume oil are collected from the cyclone.

If Example 2A and 2B are cured in an oven at 165° C. for 15 minutes, one finds that Example 2A dissolves completely in water (0.10 grams of powder in 9.9 grams of water), while Example 2B does not dissolve in water. To provide water insolubility properties to the powder, it is necessary to add the components into the slurry that is spray dried. Admixing dry ingredients does not work effectively to reduce water solubility of the powder.

Example 3

Starch Encapsulated Perfume with Acid, Catalyst, and Silica 88.75 g of HICAP 100 modified starch (Ingredion) is added to 266.25 g of water at 24° C. to make approximately a 25% wt. % solution.

The mixture is agitated at 600 RPM using a RW20 digital mixer with a turbine, 4-pitched blade impeller 2 inches in diameter, for 20 minutes.

88.75 g perfume oil is added near the vortex of the starch solution.

The emulsion formed is agitated for an additional 20 minutes (at 600 RPM).

Upon achieving a perfume droplet median volume average diameter of less than 5 microns, 15 grams of citric acid, and 7.5 grams of sodium hypophosphite monohydrate (Aldrich) is added to the emulsion. After mixing for 5 minutes, the emulsion is pumped to a spray drying tower and atomized using a centrifugal atomizer with co-current airflow for drying. The inlet air temperature is set at 205-210° C., the exit air temperature is stabilized at 98-103° C. Dried particles of the starch encapsulated perfume oil are collected from the cyclone.

Approximately 0.1 grams of AEROSIL R318 flow agent is added to the 9.9 grams of spray-dried powder. The powder is shaken to mix for 1 minute or until a free flowing powder is achieved. Gentle mixing in a rotary mixer, drum mixer, blender, or similar dry blending unit operation can be used to sufficiently mix the flow aid with the spray dried powder.

Example 4

Starch Encapsulated Perfume with Acid, Catalyst, and Silica—Curing Conditions To 99 grams of the powder of Example 3 is added 1 gram of AEROSIL R812 fumed silica, and mixed by hand agitating the jar for 1 minute to achieve a free flowing powder. The mixed powder is placed in an aluminum foil dish and the dish with powder placed into an oven to effect polysaccharide crosslinking. The cured powder (conditions shown below) is then tested for dissolution in water. The solubility of the powder is tested by suspending 0.1 g powder in 9.9 g water to achieve a 1% (w/w) solution. The solution is mixed at 250 rpm with a stir bar, for 1 hour at 20° C. A pre-weighed 3 inch diameter circle of black 100% cotton fabric is placed in a Buchner funnel attached to a vacuum line. 2 mL of the solution is then poured through the fabric, followed by a wash of 2 mL water. The fabric is allowed to air dry overnight at 22° C. The dried fabric visual residue is characterized by Scanning Electron Microscopy (SEM), and perfume odor is tested after rubbing the dried fabric. The results for nine tests (Examples 4A-4I) are tabulated in Table 1 below.

TABLE 1

Curing Condition Test Results

| Example | Powder cross-link conditions | | 0.1 g powder in 9.9 g water Observations | SEM Observations | Fragrance of fabric after 1 day drying at 22° C. |
|---|---|---|---|---|---|
| 4A | 22° C. | Not Applicable | Translucent | none | None |
| 4B | 120° C. | 15 min | Translucent | agglomerates, few particles | None |
| 4C | 135° C. | 15 min | Translucent | few deflated particles, no film | Low |
| 4D | 150° C. | 15 min | Powder settles | deflated particles, film | moderate |
| 4E | 165° C. | 15 min | Powder settles | Large qty of film and particles on fabric | High |
| 4F | 150° C. | 30 min | Powder settles | Large qty of film and particles on fabric | High |
| 4G | 150° C. | 45 min | Powder settles | Large qty of film and particles on fabric | High |
| 4H | 150° C. | 60 min | Powder settles | Large qty of film and particles on fabric | High |
| 4I | 165° C. | 15 min | Powder settles | Lage qty of film and particles on fabric | High |

Figure 1B:
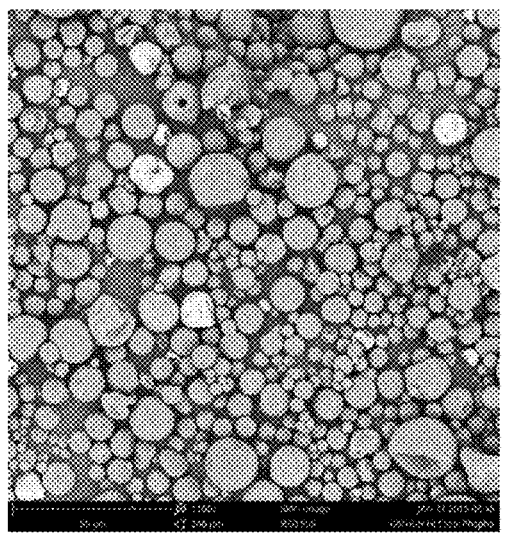
Figure 1C:
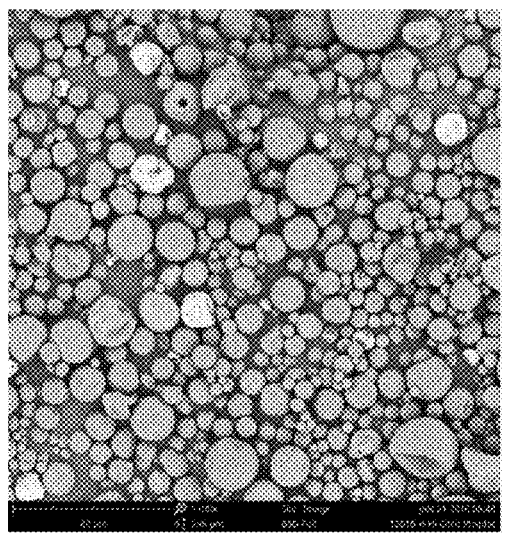

FIG. 1A is a photograph of the fabrics of Examples 4A (left) and 4I (right). SEM images are shown in FIGS. 1B and 1C. FIG. 1B shows Example 4A. FIG. 1C shows Example 4I.

Example 5

Silica Flow Agent Study

The pre-weighed flow agent is added to the specified amount of spray-dried powder of Example 2 (see Table 2 below). The powders are shaken to mix for 2 minutes. (Any suitable dry mixing method can be used.) The mixed powder is placed in an aluminum foil dish and the dish with powder placed into a 165° C. oven for 15 minutes to achieve insolubility of the particle.

To test powder flow, the angle of repose test is used. A funnel is fixed at a height of 2.5 cm above a base of set diameter. A fixed amount of powder is flowed through the funnel, and the height of the resulting powder cone is measured. Alpha values shown in Table 2 below are determined from the equation $\tan(\alpha) = \text{height}/(0.5 \times \text{base diameter})$.

TABLE 2

Silica Flow Results

| Example | Formula | CL | Powder quality | Angle of repose (°) | Flow rating |
|---|---|---|---|---|---|
| 5A | Spray-dried powder | RT | Not free flowing | 43 | Passable |
| 5B | Spray-dried powder with 1% (w/w) zeothix 18771 | 165° C., 15 min | improved flow, but not free-flowing | Does not flow | Fail |
| 5C | Spray-dried powder with 5% (w/w) zeothix 18771 | 165° C., 15 min | improved flow, but not free-flowing | Does not flow out of the funnel | Fail |
| 5D | Spray-dried powder with 10% (w/w) zeothix 18771 | 165° C., 15 min | close to free-flowing powder | Does not flow out of the funnel | Fail |
| 5E | Spray-dried powder with 1% (w/w) Syloid 244, RT | 165° C., 15 min | improved flow, but not free-flowing | Does not flow out of the funnel | Fail |
| 5F | Spray-dried powder with 5% (w/w) Syloid 244 | 165° C., 15 min | Significant increase in flow | 32 | Passes |
| 5G | Spray-dried powder with 1% (w/w %) Aerosil R 812 | RT | Fully free-flowing | 25 | Excellent |
| 5H | Spray-dried powder with 1% (w/w %) Aerosil R 812 | 165° C., 15 min | Free-flowing powder, identical to prior to baking. No noticeable color change | 25 | Excellent |

Particle agglomeration is noted after curing when the powder is cured in the absence of silica flow aid, indicating that particle bridging occurs. Addition of flow agent acts to keep the particle separate during the curing process, minimizing particle-to-particle bridging, and yielding a free flowing powder after curing.

Figure 2A:
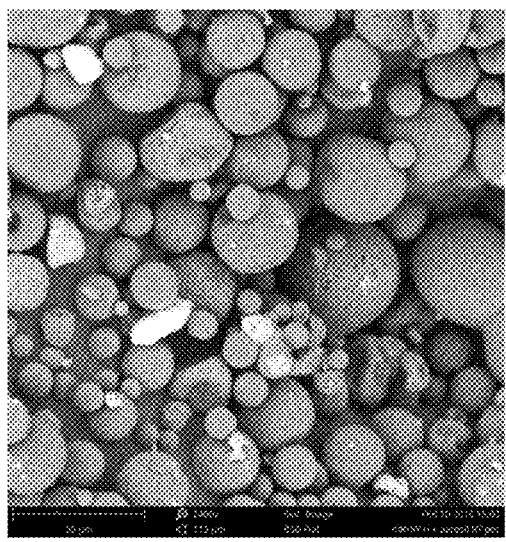
Figure 2B:

FIGS. 2A and 2B show SEM images of Examples 5G and 5H, respectively.

Example 6A

Proof of Crosslinking

Figure 3:
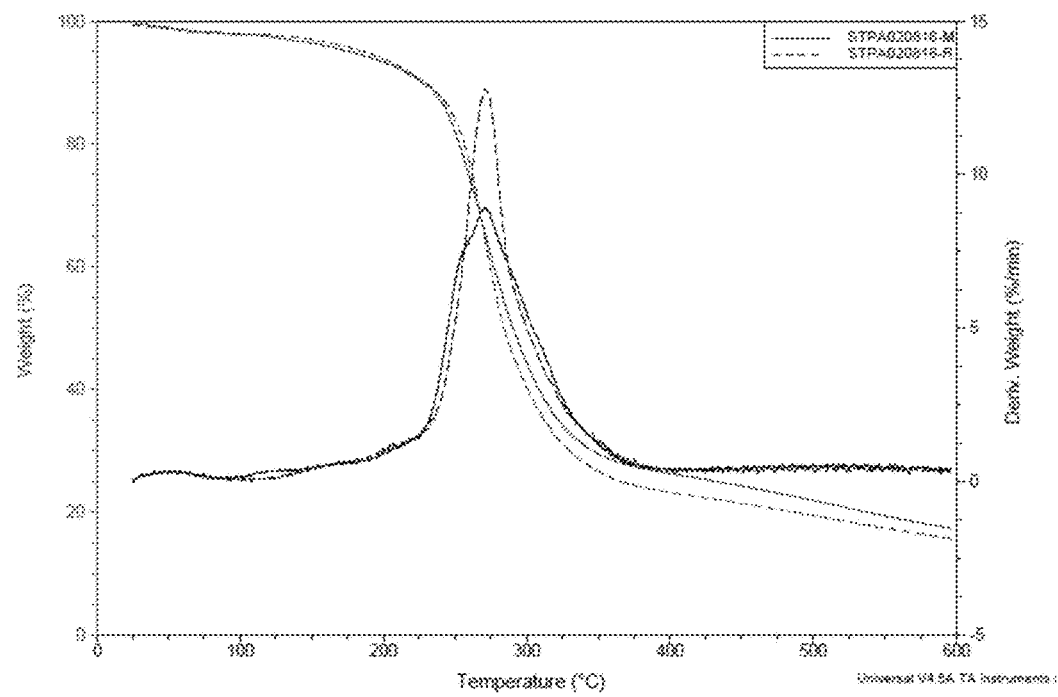

Thermal Gravimetric Analysis (TA Instruments TGAQ500) of the powder (not cured Example 5G vs. cured at 165° C./15 minutes Example 5H) shows a similar weight loss profile, suggesting that little to no perfume oil is lost from the particle during the curing process. See FIG. 3, wherein the solid lines represent Example 5G and the dashed lines represent Example 5H.

Powders were incorporated into water, and mixed for 60 minutes at 20° C. (250 RPM). 2 mL of each solution was then filtered through a black colored, 100% cotton fabric using a Buchner funnel assembly attached to a vacuum line. 2 mL of water is used to rinse the fabric. The fabric is allowed to dry overnight. Visual observations, olfactive assessment of the fabrics, and scanning electron microscopy observations are summarized in Table 3 below. A small piece of fabric is cut from the area through which the solution was flowed in the prior step, and mounted on an SEM stub. The sample is incubated in a vacuum desiccator overnight to remove volatiles and subsequently viewed in the SEM [settings: 5 kV].

TABLE 3

Results of Water Testing

| Example | Visual observations | Olfactive Assessment of Fabrics | | SEM Observations |
|---|---|---|---|---|
| 5G | complete dissolution | very little smell | capsules intact | Some intact particles |
| 5H | insolubles | smells when rubbed | capsules intact | agglomerated particles |

It is clearly evident that even after exposing the cured particles to water, the filtered particles display a noticeable amount of fragrance upon rubbing.

Powders were incorporated into 1 wt. % TIDE CLEAN BREEZE dry powder detergent solution in water, and mixed for 60 minutes at 33.3° C. (250 RPM). 2 mL of each solution was then filtered through a black colored, 100% cotton fabric using a Buchner funnel assembly attached to a vacuum line. 2 mL of water is used to rinse the fabric. The fabric is allowed to dry overnight. Visual observations, olfactive assessment of the fabrics, and scanning electron microscopy observations are summarized in Table 4 below. A small piece of fabric is cut from the area through which the solution was flowed in the prior step, and mounted on an SEM stub. The sample is incubated in a vacuum desiccator overnight to remove volatiles and subsequently viewed in the SEM [settings: 51 kV].

TABLE 4

Results of Detergent Testing

| Example | Solution Appearance | Fabric Appearance | Fragrance: panelist 1 | Fragrance: panelist 2 | SEM appearance |
|---|---|---|---|---|---|
| 5G | dispersed in water | Few particles | + | + | particles |
| 5H | evidence of insolubility | Many particles | +++ | +++ | thick film on top of fabric |

It is clearly evident that even after exposing the cured particles to detergent solution, the filtered particles display a noticeable amount of fragrance upon rubbing.

Differential Scanning Calorimetry (TA Instruments DSC Q2000) was used to confirm any thermal transitions and crosslinking phenomena that occur when heating the spray dried powder containing modified starch, perfume, citric acid, and sodium hypophosphite monohydrate.

Figure 4:
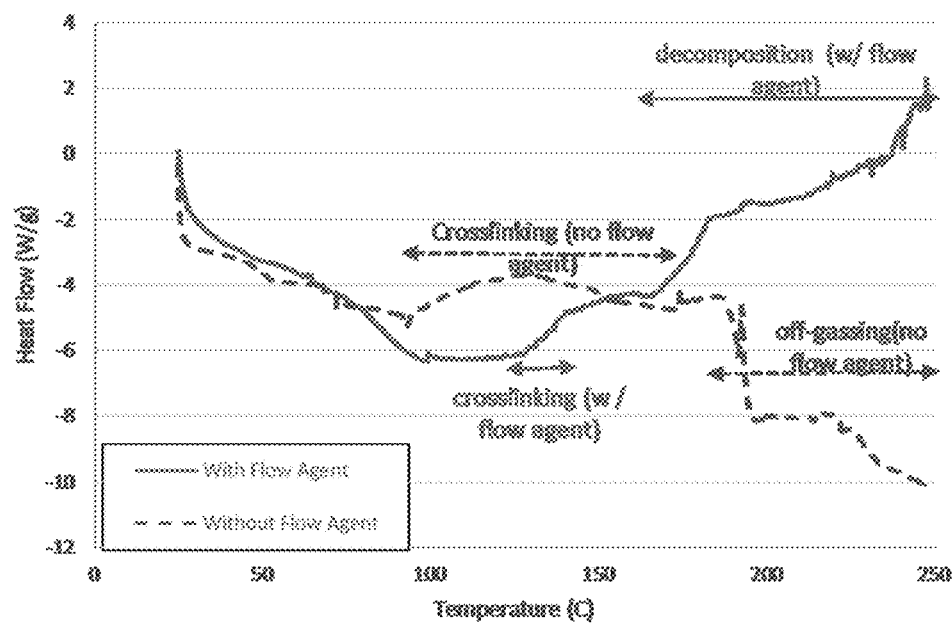

FIG. 4 shows a DSC Thermogram of powder with (Example 5H) and without (Example 5G) added fumed silica.

Figure 5:
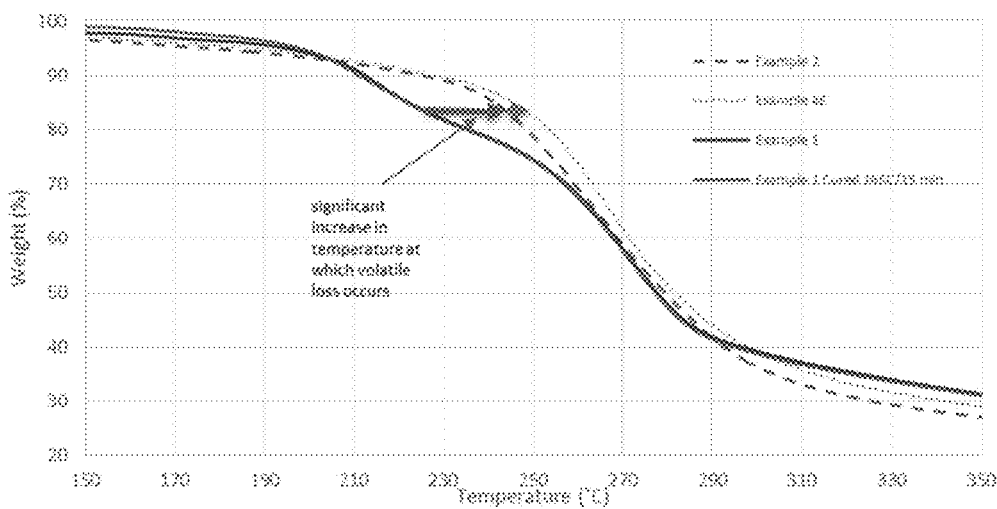

Thermal Gravimetric Analysis also shows that the addition of citric acid, hypoposhite, and silica have a unique effect on the microcapsules. These materials act to reduce the quantity of volatiles that are lost as a function of temperature—indicating a reduced permeability of the matrix through which the perfume can diffuse out (the total weight loss from each sample is the same; however, the temperature profile of that loss is very different when adding the inventive components). When citric acid and hypophosphite are incorporated into the particle, and the powder is then heated, there is a significant decrease in the volatility of the encapsulated material, an indication of reduced diffusion of the volatile active, an indication of crosslinking. Moreover, the incorporation of silica into the powder further reduces the volatility of the encapsulated active (i.e., a higher temperature is required to achieve the same mass loss via the incorporation of citric acid, hypophosphite and silica). See FIG. 5.

Example 6B

Necessary Components for Oil-Water Interfacial Interaction

Epoxidized soybean oil (Spectrum Chemicals) is soluble in perfume oil. Heating the perfume oil and epoxidized soybean oil (5 wt. % in perfume oil) at 150° C. for 30 minutes does not lead to any degradation of the perfume oil. Hence, one could not only achieve crosslinking of the polysaccharide on the aqueous side (via the use of citric acid and hypophosphite discussed in the previous examples), but also achieve an interaction at the oil-water interface that can reduce the diffusion of the encapsulated oil out of the particle. Film studies were done in order to understand the necessary compositional elements to achieve this interfacial interaction. Tabulated in Table 5A below are the amounts of various ingredients in seven different compositions. HICAP 100 starch solution was made by dissolving 25 grams of HICAP 100 (Ingredion) in 75 grams of water. Chitosan solution was made by dissolving 3 grams of Chitosan (TCI) in 97 grams of acidified water at pH 2.1 with agitation at 85° C. for 30 minutes to obtain a clear solution. The bottom two rows show the results of solubility testing of particles prepared from the compositions. From the experiments, one can infer that three components are necessary to achieve the desired interaction: an amine-functionality containing material, a hydroxyl containing material, and an epoxidized oily material.

TABLE 5A

Oil-Water Interfacial Testing

| Material | LOT INFO | Activity % | STJD050616-C | STJD050616-D | STJD050616-E | STJD050616-F | STJD050616-G | ST050616-H | ST050616-J |
|---|---|---|---|---|---|---|---|---|---|
| Perfume Oil | | 100% | 0.000 | 0.000 | 0.000 | 0.000 | 0 | 0 | 0 |
| Epoxidized Soybean Oil | Spectrum 2FC0475 | 100% | 0.380 | 0.541 | 0.340 | 0.359 | 0 | 0.407 | 0.368 |
| HICAP 100 Starch Powder | Ingredion CD16596 | 100% | 6.938 | 0.000 | 0.000 | 0.000 | 0 | 0 | 0 |
| HICAP 100 Starch Solution | Ingredion CD16596 | 25% | 0.000 | 38.026 | 27.749 | 27.240 | 27.47 | 27.34 | 0 |
| Glycerine | Sigma BCBQ5800V | 100% | 2.704 | 0.000 | 2.762 | 2.705 | 2.71 | 0 | 0 |
| Chitosan Solution | TCI C2395 | 3% | 0.000 | 0.000 | 0.000 | 6.671 | 6.89 | 6.67 | 6.72 |
| | | 150 C./30 min Cured Films | Soluble in water | Soluble in water | Soluble inwater | Insoluble in water (2.5 hrs) | Soluble in water | Insoluble in water | Soluble in water |
| | | 22 C. Aged Films Overnight | Soluble in water | Soluble in water | Soluble inwater | Soluble in water | Soluble in water | Insoluble in water | Soluble in water |

Example 6C

Using Natural Materials 222.20 grams of Capsul TA (Ingredion Corp) was dissolved in 666.5 grams of water to make a 25 wt % solution. To the Capsul TA solution is added 37.57 grams of citric acid (ADM), and 18.92 grams of sodium hypophosphite (Special Material Co). These materials are mixed for 16 minutes at 550 RPM using a 3-blade pitched turbine agitator using a IKA RW20 digital mixer. Next, 224.25 grams of Vitamin E oil is added, emulsified for 3 minutes at 20,000 RPM using Unidrive X1000. The emulsion is spray dried at an inlet air temperature of 380 to 400 degrees Fahrenheit, an outlet air temperature of 175 to 195 degrees Fahrenheit. Aerosil R812 flow aid was added to the spray dried powder at a level of 1.5 wt %, then the powder was cured in an oven at 150° C. for 30 minutes. Fabric Dissolution Test showed significant residue (indicating little to no dissolution in 1 wt % detergent solution, and successful crosslinking to render the particle insoluble). Hence, natural materials such as Tapioca starch, can also be used to achieve the same type of crosslinking and water insolubility profile as achieved with modified starches.

Example 6D

Using Hydrophobic Active Modifiers 1250 grams of HICAP 100 powder is added to 3753 grams of water, and mixed using a 3-blade marine propeller shaft, IKA RW20 digital mixer at 510 RPM for 8 minutes. The solution is allowed to deaerate overnight to provide HICAP 100 Stock Solution. To 4700 grams of HICAP 100 Stock Solution is added 200 grams of Citric Acid, and 100 grams of sodium hypophosphite and the contents are mixed for 16 minutes at 510 RPM to achieve a homogeneous Solution B. Next, several hydrophobic active oil phases are prepared, and these hydrophobic oil phases were added to Solution B (oil phase at 72 degrees Centigrade, and Solution B at 72 Degrees Centigrade), while mixing at 20,000 RPM for 4 minutes using a Unidrive X1000 rotor-stator mixer, as shown in Table 5B below.

TABLE 5B

| Hydrophobic Material | Supplier | A | B | C | D | E | F | G |
|---|---|---|---|---|---|---|---|---|
| Perfume Oil | Spray-Tek | 76.15 | 75.45 | 75.52 | 75.45 | 75.45 | 75.45 | 75.45 |
| Candelilla Wax | Strahl & Pitsch | 13.3 | | | | | | |
| Carnauba Wax | Strahl & Pitsch | | 13.31 | | | | | 3.99 |
| Rice Bran Wax | Strahl & Pitsch | | | 13.31 | | | | |
| Soya Wax | Strahl & Pitsch | | | | | 13.31 | | 9.32 |
| Hydrogenated Soya Wax | Strahl & Pitsch | | | | | | 13.32 | |
| Silicone Gum | Krayden | | | | 13.18 | | | |
| Solution B | Spray-Tek | 378 | 377 | 378 | 378 | 377 | 378 | 378 |

The emulsions were then spray dried using a 2-fluid nozzle, an inlet air temperature of 380 to 400 degrees Fahrenheit, an outlet air temperature of 175 to 195 degrees Fahrenheit. Aerosil R812 flow aid was added to the spray dried powders at a level of 1.5 wt %, then the powders were cured in an oven at 150° C. for 30 minutes. Fabric Dissolution Test showed significant residue (indicating little to no dissolution in 1 wt % detergent solution, and successful crosslinking to render the particle insoluble). Overnight drying of the fabrics, and subsequent olfactive evaluation confirmed the presence of retained fragrance oil via a highly impactful fragrance odor detected upon rubbing the fabric.

Example 7

Interfacial Polymerization with Chitosan 1250 grams of HICAP 100 powder is added to 3753 grams of water, and mixed using a 3-blade marine propeller shaft, IKA RW20 digital mixer at 510 RPM for 8 minutes. The solution is allowed to deaerate overnight to provide HICAP 100 Stock Solution. 14 grams of Acetic Acid (VWR-0714) and 26.7 grams of HCl (VWR) are added to 1945 grams of water at 85° C. to achieve a pH of 2.1. Next 60 grams of Chitosan (TCI) is added and mixed for 60 minutes at 85° C. to achieve a clear homogeneous solution. The solution is left overnight to cool. This is Chitosan Stock Solution. The next day, 5.97 grams of epoxidized soybean oil (Spectrum Chemicals) is added to 119.62 grams of perfume oil. A miscible, homogeneous solution is obtained after mixing for 1 minute. The perfume oil solution is added to 478 grams of HICAP 100 stock solution and mixed at 900 RPM for 3 minutes. Next, the emulsion is homogenized using a Unidriver X1000 at 20,000 RPM for 3 minutes to achieve an oil droplet size less than 1 micron. Finally, 167 grams of a 3 wt. % Chitosan stock solution is added to the perfume oil emulsion. The emulsion is then spray dried within 3 hours of making using a co-current spray dryer, centrifugal atomizer, inlet air temperature is set at 205-210° C., the exit air temperature is stabilized at 98-103° C. Dried particles of the starch encapsulated perfume oil particles are collected from the cyclone.

Example 8

Figure 6A:
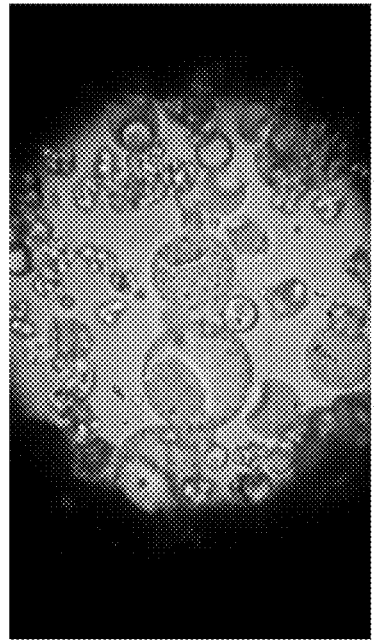
Figure 6B:
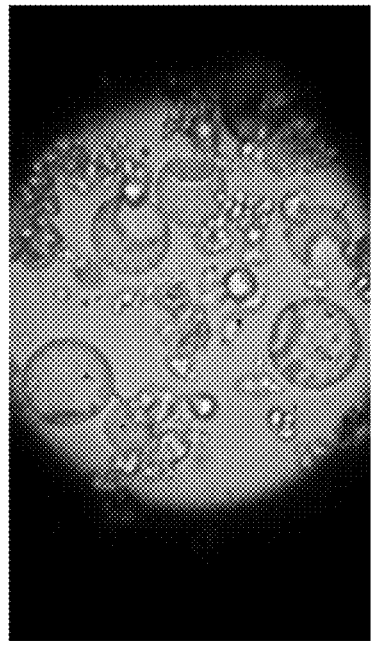

Interfacial Polymerization with Whey Protein 1250 grams of HICAP 100 powder is added to 3753 grams of water, and mixed using a 3-blade marine propeller shaft, IKA RW20 digital mixer at 510 RPM for 8 minutes. The solution is allowed to deaerate overnight to provide HICAP 100 Stock Solution. 100 grams of whey protein (St. Charles Trading Company) is added to 900 grams of water, and agitated at 510 RPM for 10 minutes using a IKA RW20 agitator and 3-blade marine propeller shaft. The solution is left overnight in a refrigerator. This is Whey Protein Stock Solution. The next day, 10.4 grams of epoxidized soybean oil (Spectrum Chemicals) is added to 207 grams of perfume oil. A miscible, homogeneous solution is obtained after mixing for 1 minute. The perfume oil solution is added to 830 grams of HICAP 100 stock solution and mixed at 900 RPM for 3 minutes. Next, 748 grams of whey protein solution is added to the emulsion, and the emulsion is heated from 29° C. to 80° C. over a period of 40 minutes, held at 80° C. for 1 hour, and then cooled to room temperature over 15 minutes. Optical microscopy clearly shows the presence of microcapsules. See FIGS. 6A and 6B.

The emulsion is then spray dried within 3 hours of making using a co-current spray dryer, centrifugal atomizer, inlet air temperature is set at 205-210° C., the exit air temperature is stabilized at 98-103° C. Dried particles of the starch encapsulated perfume oil particles are collected from the cyclone.

Example 9

Combination of Crosslinking Approaches with Chitosan 1250 grams of HICAP 100 powder is added to 3753 grams of water, and mixed using a 3-blade marine propeller shaft, IKA RW20 digital mixer at 510 RPM for 8 minutes. The solution is allowed to deaerate overnight to provide HICAP 100 Stock Solution. 14 grams of Acetic Acid (VWR-0714) and 26.7 grams of HCl (VWR) is added to 1945 grams of water at 85° C. to achieve a pH of 2.1. Next 60 grams of Chitosan (TCI) is added and mixed for 60 minutes at 85° C. to achieve a clear homogeneous solution. The solution is left overnight to cool. This is Chitosan Stock Solution. The next day, 5.35 grams of epoxidized soybean oil (Spectrum Chemicals) is added to 107.5 grams of perfume oil. A miscible, homogeneous solution is obtained after mixing for 1 minute. A mixture comprising 425.5 grams of HICAP 100 stock solution, 17.98 grams of citric acid (ADM), and 8.99 grams of Sodium Hypophosphite Monohydrate (Sigma) is prepared by mixing for 16 minutes 830 RPM 4-blade pitched turbine shaft, RW20 IKA agitator. The perfume oil solution is added to the acidified starch solution 750 RPM/3 minutes. Next, the emulsion is homogenized using a Unidriver X1000 at 20,000 RPM for 3 minutes to achieve an oil droplet size less than 1 micron. Finally, 167 grams of a 3 wt. % CHITOSAN stock solution is added to the perfume oil emulsion. The emulsion is then spray dried within 3 hours of making using a co-current spray dryer, centrifugal atomizer, inlet air temperature is set at 205-210° C., the exit air temperature is stabilized at 98-103° C. Dried particles of the starch encapsulated perfume oil particles are collected from the cyclone.

Example 10

Combination of Crosslinking Approaches with Whey

To 777 grams of the perfume microcapsules of Example 8 are added 15.2 grams of citric acid (ADM) and 7.6 grams of sodium hypophosphite monohydrate, and mixed at 500 RPM for 10 minutes. The emulsion is then spray dried within 3 hours of making using a co-current spray dryer, centrifugal atomizer, inlet air temperature is set at 205-210° C., the exit air temperature is stabilized at 98-103° C. Dried particles of the starch encapsulated perfume oil particles are collected from the cyclone.

Example 11

SEM and Gravimetric Analyses

Fumed silica Aerosil R812 was added to particles of Examples 7 through 10 in the amounts shown in Table 6 below.

TABLE 6

Fumed Silica Compositions

| Example | Particle Preparation (Example No.) | Powder (g) | Aerosil R812 (g) |
|---|---|---|---|
| 11A | 7 | 20.161 | 0.324 |
| 11B | 9 | 10.000 | 0.178 |
| 11C | 8 | 5.016 | 0.088 |
| 11D | 10 | 9.952 | 0.157 |

Next, approximately 10 grams of each of the above powders was cured by placing the powder on an aluminum foil pan, placing it an oven preset at 150° C., and left in the oven for 30 minutes. These powders were then characterized in three ways following the treatment:
 1) Scanning Electron Microscopy to understand morphology;
 2) Dispersion in 1 wt. % Tide powder detergent solution at 33.3° C. for 30 minutes, and then filtration through a 100% cotton fabric and assessment by Scanning Electron Microscopy to understand the structures that are deposited on the fabric; and
 3) Thermal Gravimetric Analysis to understand that loss of volatiles.

Scanning Electron Microscopy of the cured particles show that incorporation of citric acid and catalyst smoothens the surface, reduces the pores, and causes some aggregation of particles. Compare Example 11B (citric acid and catalyst) with Example 11A (control) and Example 11D (citric acid and catalyst) with Example 11C (control).

Figure 7A:
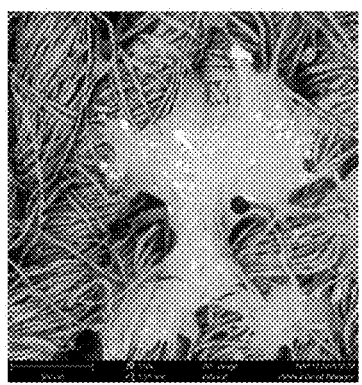
Figure 7B:
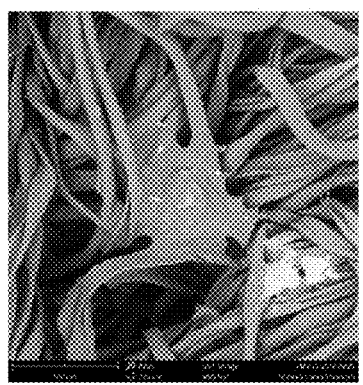
Figure 7C:
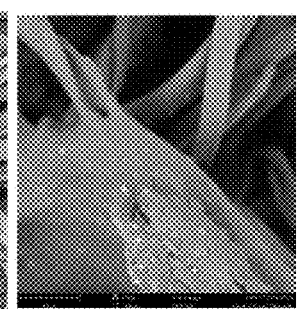
Figure 8A:
Figure 8B:
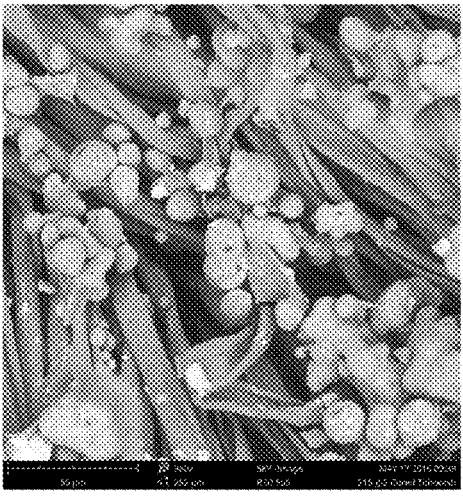
Figure 8C:
Figure 8D:
Figure 9A:
Figure 9B:
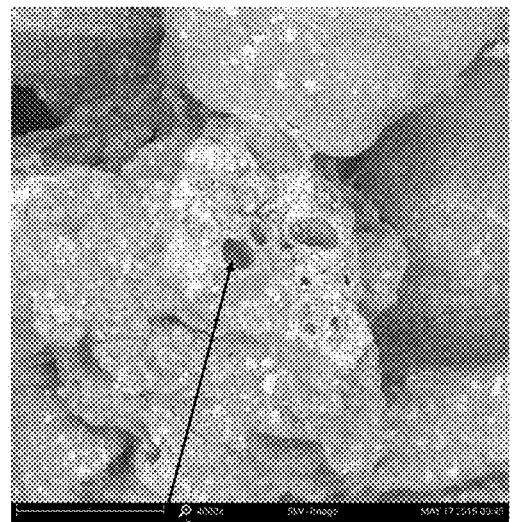
Figure 9C:
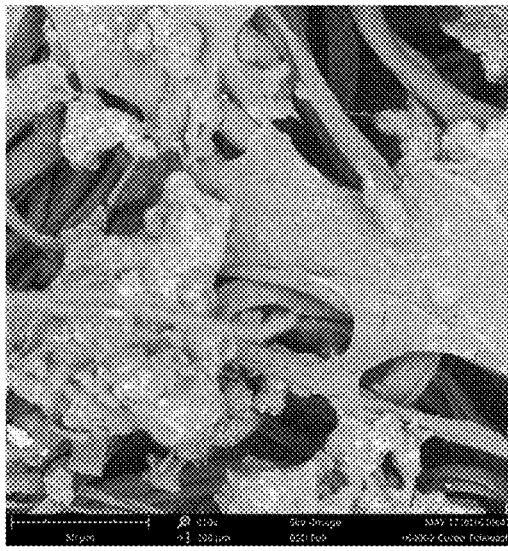
Figure 9D:
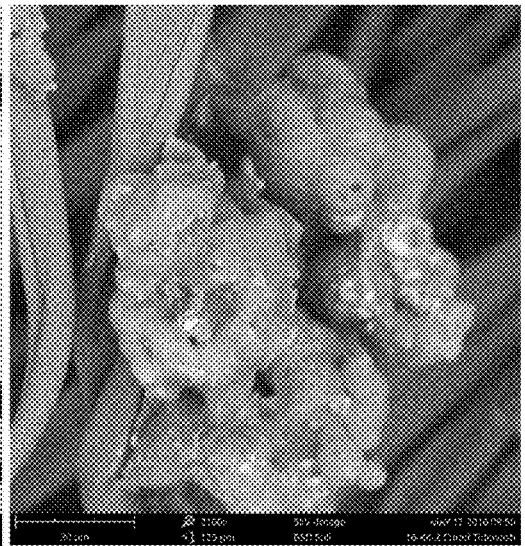

Surprisingly, intact particles are observed only in specific cases, after exposure to detergent solution. FIGS. 7A, 7B and 7C are SEM images of the fabric of Example 11A at 210×, 820× and 1950× magnification, respectively. The images show film deposits on the fabric. No particles are observed. Despite forced filtration through a Buchner assembly, the density of the deposition is not very high.

FIGS. 8A, 8B, 8C and 8D are SEM images of the fabric of Example 11B at 255×, 960×, 1500× and 950× magnification, respectively. The images show a high density of particle deposition on fabric, wherein intact, spherical particles are coated by a polymer glue/film.

FIGS. 9A, 9B, 9C and 9D are SEM images of the fabric of Example 11C at 860×, 4000×, 910× and 2100× magnification, respectively. After spray drying, exposure to detergent solution and filtration onto fabric, film deposits are observed on the fabric with intact particle aggregates having low surface porosity. The density of particles deposited on the fabric is high. The arrow of FIG. 9B points out that the deposit has a crevice 100 with the same morphology as capsules observed under optical microscope before spay drying.

Figures 10A, 10B, 10C:
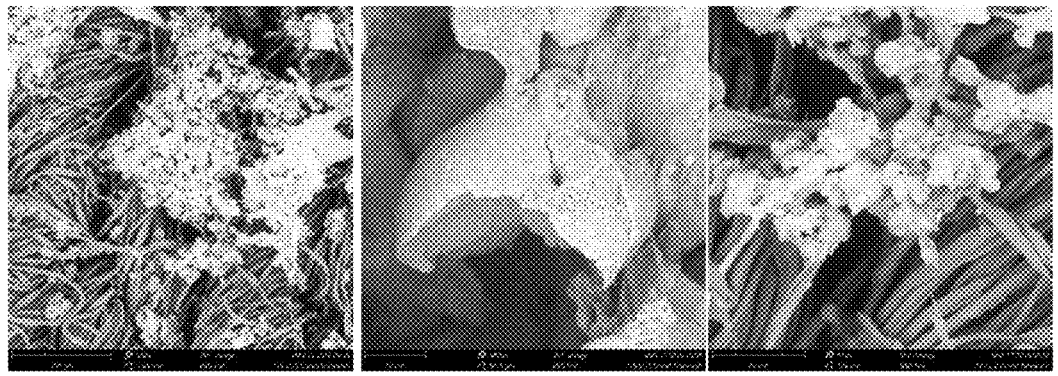

FIGS. 10A, 10B and 10C are SEM images of the fabric of Example 11D at 260×, 4800× and 910× magnification, respectively. The images show film and particle deposits on the fabric. Matrix morphology on the interior of the capsules is observed.

Thus, the particles of Example 7 are no longer visible on fabric after exposure to detergent (Example 11A). However, the particles of Examples 8, 9, and 10 (Examples 11B, 11C and 11D) all show intact particles on fabric despite exposure to surfactant solution.

Thermal Gravimetric Analysis is a tool that can help understand the profile of volatiles that are lost as a function of temperature. A reduction in the mass loss of a particle vs. temperature is an indication of higher degree of crosslinking (whether it is physical or chemical), as this crosslinking will provide a more tortuous path for the volatile material to diffuse through the encapsulating matrix.

Figure 11:
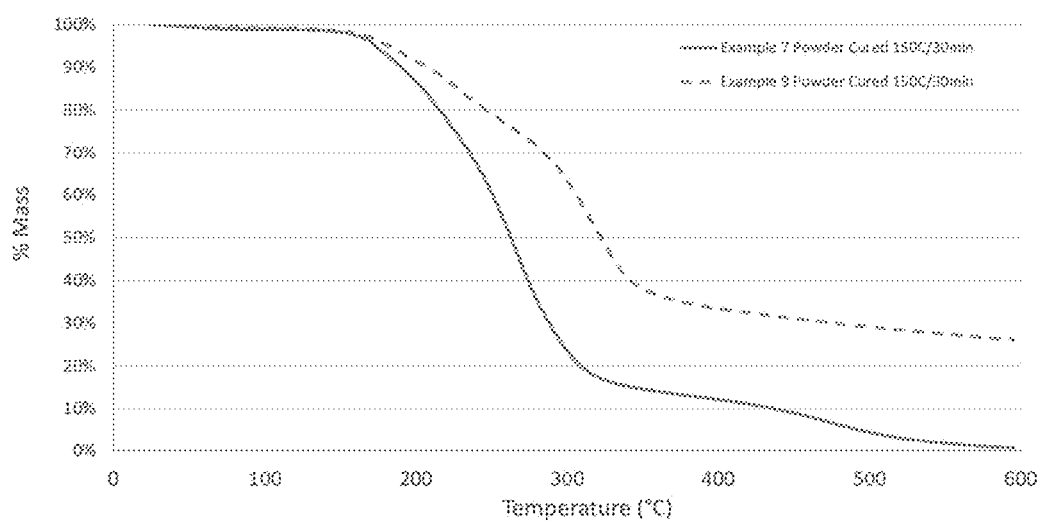
Figure 12:
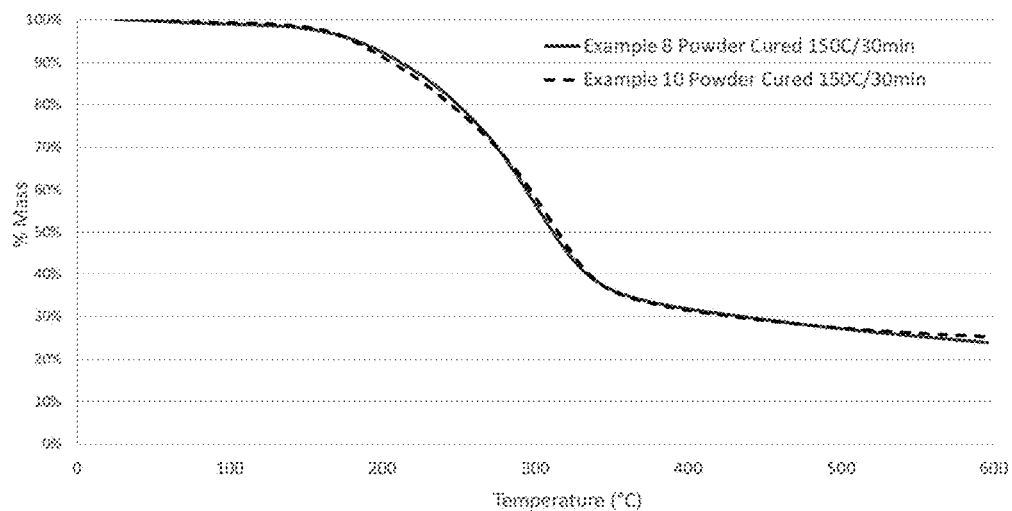

FIG. 11 shows that the incorporation of citric acid and catalyst in the aqueous phase leads to lower volatile loss with a chitosan/epoxidized soybean oil matrix. FIG. 12 shows that the incorporation of citric acid and catalyst in the aqueous phase of a whey/epoxidized soybean oil matrix does not lead to any change in the volatile loss.

Figure 13:
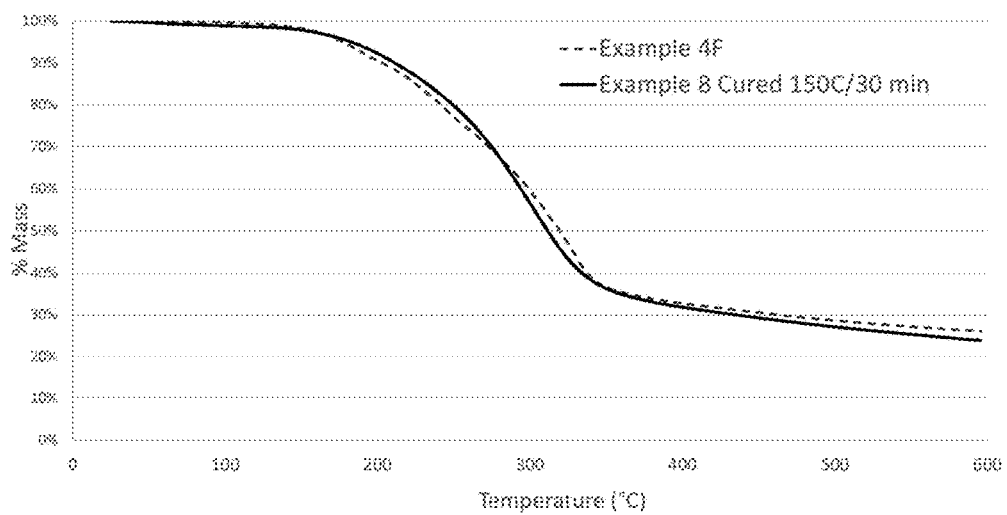

The volatile loss observed with whey/epoxidized soybean oil/starch particle is identical to that observed with starch/citric acid/catalyst matrix. See FIG. 13. That is, the interfacial polymerization is excellent with whey. Additional crosslinking in the aqueous phase does not really add an additional diffusion barrier. The presence of intact particles on fabric even after exposure to detergent confirms the interfacial polymerization reaction robustness to restrict perfume diffusion.

Example 12

Olfactive Analyses

The grading scale of Table 7 below was used for olfactive analyses.

TABLE 7

Olfactive Grading Scale

| 0 | No smell |
|---|---|
| 1 | Faint fragrance |
| 2 | Noticeable fragrance |
| 3 | Strong fragrance |

Deodorant

The cured powder of Example 5H is incorporated into various "unscented" commercially available products, heated to 85° C., to deliver approximately 1 wt. % perfume oil loading into the "unscented" product. The product is then stored at 40° C. for 72 hours. The aged product is applied (0.5 g) to fabric swatches and dried in air for 24 hours. The fabric swatches are then rubbed and the fragrance level compared to control samples not containing the cured powder. Table 8 below shows the results.

TABLE 8

Deodorant Test Results

| Product | Mfr | Product Code | Lot | Fragrance Level Before Rubbing | Fragrance Level After Rubbing |
|---|---|---|---|---|---|
| TOM'S OF MAINE, UNSCENTED DEODORANT | Tom's of Maine | P9889659 | 6022UST11A | 1 | 2.5 |
| SURE, UNSCENTED INVISIBLE SOLID (APDO) | Idelle Labs | SUU71717 LBL F03 | 15260 B2 | 0.5 | 2 |
| DOVE, ADVANCED CARE SENSITIVE ANTIPERSPIRANT | Unilever | 83262209 | 02156UR05 | 0.5 | 2 |
| MITCHUM, SENSITIVE SKIN FRAGRANCE FREE (APDO) | Revlon | 055611-52 | 15323 | 1 | 2.5 |

Bar Soap

The cured powder of Example 5H is incorporated into commercially available products to deliver approximately 1 wt. % perfume oil into each unscented bar soap (heated to 85° C. to reduce the viscosity and allow sufficient mixing). The bar soap is then stored at 40° C. for 72 hours. The aged product is applied (0.1 g) to a wet fabric swatch. The fabric swatches are then rubbed and the fragrance level compared to control samples (not containing the cured powder). See Table 9 below.

TABLE 9

Bar Soap Test Results

| Product | Manufacturer | Product Code | Lot | Fragrance Level |
|---|---|---|---|---|
| OLAY BAR SOAP, MOISTURE OUTLAST, SENSITIVE | P&G | 97393622 | 5320U1A1 | 1 |

TABLE 9-continued

Bar Soap Test Results

| Product | Manufacturer | Product Code | Lot | Fragrance Level |
|---|---|---|---|---|
| IVORY BAR SOAP | P&G | | 6049U16B | 0 |
| DOVE BAR SOAP, SENSITIVE SKIN BEAUTY BAR | Unilever | | 01216XU04 | 2.5 |
| NEUTROGENA BAR SOAP, FRAGRANCE-FREE FACIAL BAR | Neutrogena | | 0146L0119 | 2.5 |

Powder Cleanser

The cured powder of Example 5H is incorporated into a powder cleanser product to deliver approximately 1 wt. % oil into unscented powder cleanser (BON AMI POWDER CLEANSER, Bon Ami Company, 5-579-98, Lot 15February16 0858) and left at room temperature for six days. The powder (0.5 g) is placed in a weigh boat with 1 g water. The fragrance of the powder in water is noted, and compared to powder that is mechanically agitated, similar to the motion of applying a scrubbing cleaner. These are compared to the fragrance level of the dry powder with no added particles, both dry and in water. See Table 10 below.

TABLE 10

Powder Cleanser Test Results

| Sample | Agitation | Fragrance Level |
|---|---|---|
| With powder, dry | None | 1 |
| With powder, in water | None | 2 |
| With powder, in water | Scrubbing | 3 |
| Control dry | None | 0 |
| Control in water | None | 0 |
| Control in water | scrubbing | 0 |

Fabric Refresher

The cured powder of Example 5H is incorporated into FEBREZE FABRIC REFRESHER solution to deliver approximately 1 wt. % oil into FEBREZE FABRIC REFRESHER, Extra Strength (P&G, 92097855, Lot 60341731062121.00) and stored at room temperature for six days. The solution containing particles and control solution without particles is applied to 100% cotton fabric swatches and the fragrance levels compared. The results are shown in Table 11 below.

TABLE 11

Fabric Refresher Results

| | Perfume oil fragrance level | |
|---|---|---|
| Sample | 0 hours | 5 hours |
| With particles | 3 | 3 |
| Without particles | 0 | 0 |

Urine

The cured powder of Example 5H is incorporated into male urine to deliver approximately 0.5 wt % oil in the urine via the particles, at a urine temperature of 38 degrees Centigrade. The particles release fragrance at a much faster rate and intensity versus when placed in water. See Tables 12A and 12B below.

TABLE 12A

| | Perfume oil fragrance level in Urine at 38° C. | |
|---|---|---|
| Sample | 0 hours | 5 hours |
| With particles | 3 | 3 |
| Without particles | 0 | 0 |

TABLE 12B

| | Perfume oil fragrance level in water at 38° C. | |
|---|---|---|
| Sample | 0 hours | 5 hours |
| With particles | 1 | 1.5 |
| Without particles | 0 | 0 |

While not limited by theory, urine contains small levels of amylase enzyme. This enzyme is able to break down the crosslinked polymer to yield a more porous particle that releases fragrance. Separate experiments were conducted to confirm this hypothesis: approximately 1.0 grams of bacterial amylase 100,000 BAU/g (Bio-Cat Lot BA100-LZ07) was dissolved in 19 grams of deionized water. Approximately 0.10 grams of cured powder of Example H was added to 10 grams of water to make Solution A. Approximately 0.10 grams of cured powder of Example H were added to 10 grams of water to make Solution B. To solution A is added 1 gram of bacterial Amylase solution, and allowed to react at 38 degrees Centigrade for 30 minutes. 1 gram of water is added to Solution B, and allowed to sit at 38 degrees Centigrade for 30 minutes. Extraction of both solution A and B with hexane, followed by GC/MS analysis show less than 10% of the oil is extractable out of Solution B, whereas more than 70% of the oil is extractable from Solution A.

Example 13

Hair Conditioner

Selected microcapsules from the above examples are formulated into a leave-on-conditioner formulation as follows: to 98.0 grams of leave-on-conditioner (with a typical formulation given below) is added an appropriate amount of microcapsule slurry of examples 4E and 4F, to deliver an encapsulated oil usage level of 0.5 wt. %. The microcapsules are added on top of the conditioner formulation, then the contents are mixed at 1000 RPM for 1 minute.

A typical composition of a leave-on conditioner formulation is given in Table 12 below.

TABLE 12

Hair Condition Formulation

| Components | Ex. I (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18 (Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Preservatives | 0.40-0.60 |

Example 14

Shampoo

Selected microcapsules from the above examples are formulated into a rinse-off shampoo formulation as follows: to 90.0 grams of shampoo formulation (with a typical formulation given below) is added an appropriate amount of microcapsule slurry of Examples 4E and 4F, to deliver an encapsulated oil usage level of 0.5 wt. %. The microcapsules and water are added on top of the shampoo formulation, then the contents are mixed at 1850 RPM for 1 minute. Typical shampoo formulations are shown in Tables 13-15 below.

TABLE 13

Shampoo Formulations

| | Example | | |
|---|---|---|---|
| Ingredient | 14A | 14B | 14C |
| Water | q.s. | q.s. | q.s. |
| Polyquaternium 76[1] | 2.50 | — | — |
| Guar, Hydroxylpropyl Trimonium Chloride[2] | — | 0.25 | — |
| Polyquaterium 6[3] | — | — | 0.79 |
| Sodium Laureth Sulfate (SLE3S)[4] | 21.43 | 21.43 | 21.43 |
| Sodium Lauryl Sulfate (SLS)[5] | 20.69 | 20.69 | 20.69 |
| Silicone[6] | 0.75 | 1.00 | 0.5 |
| Cocoamidopropyl Betaine[7] | 3.33 | 3.33 | 3.33 |
| Cocoamide MEA[8] | 1.0 | 1.0 | 1.0 |
| Ethylene Glycol Distearate[9] | 1.50 | 1.50 | 1.50 |
| Sodium Chloride[10] | 0.25 | 0.25 | 0.25 |
| Fragrance | 0.70 | 0.70 | 0.70 |
| Fragrance Microcapsule of Example 4F | 1.2 | 1.2 | 1.2 |
| Preservatives, pH adjusters | Up to 1% | Up to 1% | Up to 1% |

[1]Mirapol AT-1, Copolymer of Acrylamide(AM) and TRIQUAT, MW = 1,000,000; CD = 1.6 meq./gram; 10% active; Supplier Rhodia
[2]Jaguar C500, MW-500,000, CD = 0.7, supplier Rhodia
[3]Mirapol 100S, 31.5% active, supplier Rhodia
[4]Sodium Laureth Sulfate, 28% active, supplier: P&G
[5]Sodium Lauryl Sulfate, 29% active supplier: P&G
[6]Glycidol Silicone VC2231-193C
[7]Tegobetaine F-B, 30% active supplier: Goldschmidt Chemicals
[8]Monamid CMA, 85% active, supplier Goldschmidt Chemical
[9]Ethylene Glycol Distearate, EGDS Pure, supplier Goldschmidt Chemical
[10]Sodium Chloride USP (food grade), supplier Morton; note that salt is an adjustable ingredient, higher or lower levels may be added to achieve target viscosity.

TABLE 14

Shampoo Formulations

| | Example | | |
|---|---|---|---|
| Ingredient | 14D | 14E | 14F |
| Water | q.s. | q.s. | q.s. |
| Silicone A[1] | 1.0 | 0.5 | 0.5 |
| Cyclopentasiloxane[4] | — | 0.61 | 1.5 |
| Behenyl trimethyl ammonium chloride[5] | 2.25 | 2.25 | 2.25 |
| Isopropyl alcohol | 0.60 | 0.60 | 0.60 |
| Cetyl alcohol[6] | 1.86 | 1.86 | 1.86 |
| Stearyl alcohol[7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/Methylisothiazolinone[8] | 0.0005 | 0.0005 | 0.0005 |
| Panthenol[9] | 0.10 | 0.10 | 0.10 |
| Panthenyl ethyl ether[10] | 0.05 | 0.05 | 0.05 |
| Fragrance | 0.35 | 0.35 | 0.35 |
| Fragrance Microcapsules (Example 4F) | 1.2 | 1.2 | 1.2 |

[1]Glycidol Silicone
[4]Cyclopentasiloxane: SF1202 available from Momentive Performance Chemicals
[5]Behenyl trimethyl ammonium chloride/Isopropyl alcohol: Genamin TM KMP available from Clariant
[6]Cetyl alcohol: Konol TM series available from Shin Nihon Rika
[7]Stearyl alcohol: Konol TM series available from Shin Nihon Rika
[8]Methylchloroisothiazolinone/Methylisothiazolinone: Kathon TM CG available from Rohm & Haas
[9]Panthenol: Available from Roche
[10]Panthenyl ethyl ether: Available from Roche

TABLE 15

Shampoo Formulations

| | Example | |
|---|---|---|
| Ingredient | 14G | 14H |
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride (1) | 0.40 | |
| Guar Hydroxypropyl trimonium chloride (2) | | 0.40 |
| Dimethicone (3) | 2.00 | 2.00 |
| Gel Network (4) | | 27.27 |
| Ethylene Glycol Distearate | 1.50 | 1.50 |
| 5-Chloro-2-methyl-4-isothiazolin-3-one, Kathon CG | 0.0005 | 0.0005 |

TABLE 15-continued

Shampoo Formulations

| Ingredient | Example 14G | Example 14H |
|---|---|---|
| Sodium Benzoate | 0.25 | 0.25 |
| Disodium EDTA | 0.13 | 0.13 |
| Perfume | 0.40 | 0.40 |
| Fragrance Microcapsules of Example 4F | 0.30 | 0.30 |
| Citric Acid/Sodium Citrate Dihydrate | pH QS | pH QS |
| Sodium Chloride/Ammonium Xylene Sulfonate | Visc. QS | Visc. QS |
| Water | QS | QS |

(1) Jaguar C17 available from Rhodia
(2) N-Hance 3269 (with Mol. W. of ~500,000 and 0.8 meq/g) available from Aqulaon/Hercules
(3) Viscasil 330M available from General Electric Silicones
(4) Gel Networks; See composition in Table 16 below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

TABLE 16

Gel Network Composition

| Ingredient | Wt. % |
|---|---|
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 15

Lotion

For the examples below, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

TABLE 17

Lotion Formulations

| Ingredient/Property | Example 15A | Example 15B | Example 15C |
|---|---|---|---|
| PHASE A | | | |
| DC-9040[1] | 8.60 | 3.00 | 5.00 |
| Dimethicone | 4.09 | 4.00 | 4.00 |
| Polymethylsilsesquioxane[2] | 4.09 | 4.00 | 4.00 |
| Cyclomethicone | 11.43 | 0.50 | 11.33 |
| KSG-210[3] | 5.37 | 5.25 | 5.40 |
| Polyethylene wax[4] | 3.54 | | 2.05 |
| DC-2503 Cosmetic Wax[5] | 7.08 | 10.00 | 3.77 |
| Hydrophobic TiO$_2$ | | | 0.50 |
| Iron oxide coated Mica | | | 0.65 |
| TiO$_2$ Coated Mica | 1.00 | 1.00 | |
| Fragrance Particles of Example 4F | 1.00 | 1.00 | 1.00 |

TABLE 17-continued

Lotion Formulations

| Ingredient/Property | Example 15A | Example 15B | Example 15C |
|---|---|---|---|
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate[6] | 0.10 | 0.10 | 0.10 |
| Niacinamide[7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning.
[2] E.g., TOSPEAR 145A or TOSPEARL 2000. Available from GE Toshiba Silicon.
[3] 25% Dimethicone PEG-10/15 Crosspolymer in Dimethicone. Available from Shin-Etsu.
[4] JEENATE 3H polyethylene wax from Jeen.
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

Example 16

Antiperspirant/Deodorant

The below example 16A can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

TABLE 18

Antiperspirant/Deodorant Formulation

| Ingredient | Example 16A |
|---|---|
| Part I: Partial Continuous Phase | |
| Hexamethyldisiloxane[1] | QS |
| DC5200[2] | 1.20 |
| Fragrance | 0.35 |
| Fragrance Capsules of Example 4F | 1.00 |
| Part II: Disperse Phase | |
| ACH (40% solution)[4] | 40.00 |
| propylene glycol | 5.00 |
| Water | 12.30 |
| Part III: Structurant Plus Remainder of Continuous Phase | |
| FINSOLVE TN | 6.50 |

QS - indicates that this material is used to bring the total to 100%.
[1] DC 246 fluid from Dow Corning
[2] from Dow Corning
[3] Standard aluminum chlorohydrate solution Examples 16B to 16E can be made as follows: all ingredients except the fragrance, and fragrance capsules are combined in a suitable container and heated to about 85° C. to form a homogenous liquid. The solution is then cooled to about 62° C. and then the fragrance, and fragrance microcapsules are added. The mixture is then poured into an appropriate container and allowed to solidify up cooling to ambient temperature.

Example 16F can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

TABLE 19

Antiperspirant/Deodorant Formulations

| | Example | | | | |
|---|---|---|---|---|---|
| Ingredient | 16B | 16C | 16D | 16E | 16F |
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragramce | 0.5 | 0.5 | 0.5 | 0.5 | 0.5 |
| Fragrance capsules of Example 4F | 1.0 | 1.0 | 1.0 | 1.0 | 0.5 |
| Propellant (1,1 difluoroethane) | | | | | 40 |

QS - indicates that this material is used to bring the total to 100%.

Example 17

Rinse-Off Conditioner

The conditioning compositions of Examples 17A through 17F are prepared as follows: cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of Example 17B is prepared as follows: cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

TABLE 20

Rinse-Off Conditioner Formulations

| | Example | | | | | |
|---|---|---|---|---|---|---|
| Ingredient | 17A | 17B | 17C | 17D | 17E | 17F[3] |
| Premix | | | | | | |
| Aminosilicone-1 [1] | 0.50 | 0.50 | | | | |
| Aminosilicone-2 [2] | | | 0.50 | 0.50 | 0.50 | |
| PDMS | | | | | | 0.50 |
| Fragrance microcapsules of Example 4F | ... | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

[1] Aminosilicone-1 (AMD): having an amine content of 0.12-0.15 m mol/g and a viscosity of 3,000-8,000 mPa · s, which is water insoluble
[2] Aminosilicone-2 (TAS): having an amine content of 0.04-0.06 m mol/g and a viscosity of 10,000-16,000 mPa · s, which is water insoluble
[3] Comparative example with PDMS instead of amino silicone Example 18

Body Cleansing Composition

TABLE 21

Body Cleansing Composition Formulations

| | Example | | |
|---|---|---|---|
| Ingredient | 18A | 18B | 18C |
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |

TABLE 21-continued

Body Cleansing Composition Formulations

| Ingredient | Example 18A | Example 18B | Example 18C |
|---|---|---|---|
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules of Example 4F | 10 | 10 | 10 |
| III: Surfactant Phase:Benefit Phase Blending Ratio | 50:50 | 90:10 | 90:10 |

Example 19

Fabric Softening Product

Non-limiting examples of product formulations containing purified perfume microcapsules of the aforementioned examples are summarized in the following table.

TABLE 22

Fabric Softening Product Formulations

| Ingredient | 19A | 19B | 19C | 19D | 19E | 19F | 19G | 19H | 19I | 19J |
|---|---|---|---|---|---|---|---|---|---|---|
| FSA [a] | 14 | 16.47 | 14 | 12 | 12 | 16.47 | 3.00 | 6.5 | 5 | 5 |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.

[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.

[g] SE39 from Wacker

[h] Diethylenetriaminepentaacetic acid.

[i] KATHON CG available from Rohm and Haas Co. "PPM" is "parts per million."

[j] Gluteraldehyde

[k] Silicone antifoam agent available from Dow Corning Corp. under the trade name DC2310.

[l] Hydrophobically-modified ethoxylated urethane available from Rohm and Haas under the tradename Aculyn™ 44.

*Suitable combinations of the microcapsules provided in Examples 4E and 4F. (Percent active relates to the core content of the microcapsule.)

Example 20

Dry Laundry Formulations

Non-limiting examples of product formulations containing purified perfume microcapsules of the aforementioned examples are summarized in the following table.

TABLE 23

Dry Laundry Formulations

| Ingredient | % w/w granular laundry detergent composition Example | | | | | | |
|---|---|---|---|---|---|---|---|
| | 20A | 20B | 20C | 20D | 20E | 20F | 20G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | QS | QS | QS | QS | QS | QS | QS |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules (Example 4F) | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

QS - as used herein indicates that this material is used to bring the total to 100%.

Example 21

Liquid Laundry Formulations (HDLs)

Non-limiting examples of product formulations containing purified perfume microcapsules of the aforementioned examples are summarized in the following table.

TABLE 24

Liquid Laundry Formulations (HDLs)

| Ingredient | Example | | | | | |
|---|---|---|---|---|---|---|
| | 21A | 21B | 21C | 21D | 21E | 21F |
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |

TABLE 24-continued

Liquid Laundry Formulations (HDLs)

| Ingredient | 21A | 21B | 21C | 21D | 21E | 21F |
|---|---|---|---|---|---|---|
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules of Example 4F | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

TABLE 25

Liquid Laundry Detergent Formulations

| Ingredient | 21G | 21H | 21I | 21J |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | 1.0 | |
| Dye | | 0.002 | 0.002 | 0.002 |
| Opacifier (Styrene Acrylate based) | 0.1 | | | |
| Bentonite Softening Clay | | 1.0 | | |
| Polyquaternium 10 - Cationic hydroxyl ethyl cellulose | 1.0 | | 1.0 | 1.0 |

TABLE 25-continued

Liquid Laundry Detergent Formulations

| Ingredient | 21G | 21H | 21I | 21J |
|---|---|---|---|---|
| PP-5495 (silicone ex Dow Corning Corporation, Midland, MI) | | 1.0 | | |
| DC 1664 (silicone ex Dow Corning Corporation, Midland, MI) | | | 1.0 | |
| Perfume micro capsules (expressed as perfume oil) of Example 4F | 0.8 | 0.5 | 1.0 | 0.7 |
| Perfume | 0.7 | 0.55 | 1.00 | 1.00 |
| Poly Ethylene Imine MW 25000 | 0.1 | | | |
| Water | Up to 100 | Up to 100 | Up to 100 | Up to 100 |

TABLE 26

Liquid Laundry Detergent Formulations.

| Ingredient | 21K | 21L | 21M |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules (expressed as perfume oil) of Example 4F | 1.6 | 1.5 | 1.4 |
| Perfume | 1.2 | 1.6 | 1.0 |
| Form. Phenyl Boronic Acid | | | Present |
| Water** | Up to 100 | Up to 100 | Up to 100 |

**Low water liquid detergent in Polyvinylalcohol unidose/sachet

Example 22

Liquid and Gel Detergents

TABLE 27

Liquid and Gel Detergent Formulations (% by Weight)

| Ingredient | 22A | 22B | 22C |
|---|---|---|---|
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2, 5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Perfume microcapsules as Example 4F | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 s$^{-1}$, cps | 2700 | 400 | 300 |

Example 23

Liquid Unit Dose

The following are examples of unit dosage forms wherein the liquid composition is enclosed within a PVA film. The preferred film used in the present examples is Monosol M8630 76 μm thickness.

TABLE 28

Unit Dose Laundry Cleaner

| | Example | | | | | | | |
|---|---|---|---|---|---|---|---|---|
| | 23A 3 compartments | | | 23B 2 compartments | | 23C 3 compartments | | |
| | Compartment # | | | | | | | |
| | 42 | 43 | 44 | 45 | 46 | 47 | 48 | 49 |
| | Dosage (g) | | | | | | | |
| | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |
| Microcapsules Example 4F | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . .) | 2.0 | 2.0 | 2.0 | 4.0 | 1.5 | 2.2 | 2.2 | 2.0 |
| Buffers (sodium carbonate, monoethanolamine)[2] | To pH 8.0 for liquids To RA > 5.0 for powders | | | | | | | |
| Solvents (1,2 propanediol, ethanol), sodium sulfate | To 100 p | | | | | | | |

[1] Polyethylenimine (MW = 600) with 20 ethoxylate groups per —NH.
[2] RA = Reserve Alkalinity (g NaOH/dose)

Example 24

Environmental Biodegradability

Microcapsules of Example 4F were evaluated for environmental biodegradability by adapting the OCDE/OECD 301D Closed Bottle Test method. 3 liters of water from a fresh river source (Lehigh River, Sand Island Access Point, Bethlehem, Pa.) was filtered through a Whatman 597 (catalog 10311808) filter using a Buchner funnel assembly. The following mineral solutions of Table 29 were made:

TABLE 29

Mineral Oil Solutions

| Mineral Solution ID | Ingredient | Formula | Mass (g) |
|---|---|---|---|
| A | Potassium dihydrogen orthophosphate | $KH_2PO_4$ | 8.50 |
| | Dipostassium hydrogen orthophosphate | $K_2HPO_4$ | 21.75 |
| | Disodium hydrogen orthophosphate dihydrate | $Na_2HPO_4$—$2H_2O$ | 33.40 |
| | Ammonium chloride | $NH_4Cl$ | 0.50 |
| | Dissolve in water and bring to 1 L. pH to 7.4 | | |
| B | Calcium Chloride anhydrous OR | $CaCl_2$ | 27.50 |
| | Calcium Chloride dihydrate | $CaCl_2$—$2H_2O$ | 36.40 |
| | Dissolve in water and bring to 1 L. | | |
| C | Magnesium sulfate heptahydrate | $MgSO_4$—$7H_2O$ | 22.50 |
| | Dissolve in water and bring to 1 L. | | |

TABLE 29-continued

Mineral Oil Solutions

| Mineral Solution ID | Ingredient | Formula | Mass (g) |
|---|---|---|---|
| D | Iron (III) chloride hexahydrate Dissolve in water and bring to 1 L. | $FeCl_3$—$6H_2O$ | 0.25 |

To 996 mL of the filtered water solution, add 1 mL each of mineral solutions A, B, C, and D. Prepare approximately 500 mL solutions containing the particles to be tested. Fill BOD bottles (500 mL capacity) just past the neck of the bottle. Insert stopper. Store BOD bottles in the dark. Use dissolved oxygen meter (YSI 5000), and YSI5905 Dissolved Oxygen meter probe to measure oxygen at specific time points.

TABLE 30

Sample preparation for biodegradability test

| Samples | Concentration (mg/L) |
|---|---|
| River Water (no particles control) | 0 |
| Tap water + particles (no microbes control) | 5 |
| River water + starch (complete biodegradation control) | 5 HiCAP 100 |
| River water + starch (complete biodegradation control) | 5 HiCAP 100 |
| River water + particles of Example 4F | 5 |
| River water + particles of Example 4F | 5 |

The dissolved oxygen measured values as a function of time are tabulated in Table 31 below.

TABLE 31

Measured dissolved oxygen concentration as a function of time

| | Temp. (deg C.) | Neg Control (no sample) Rep 1 mg/L $O_2$ | Neg Control (no bacteria) Rep 1 mg/L $O_2$ | Positive Control (starch) Rep 1 mg/L $O_2$ | Positive Control (starch) Rep 2 mg/L $O_2$ | Particles of Example 4F Rep 1 mg/L $O_2$ | Particles of Example 4F Rep 2 mg/L $O_2$ |
|---|---|---|---|---|---|---|---|
| Day 0 | 21.5 | 6.83 | 9.50 | 7.09 | 7.12 | 6.71 | 6.70 |
| Day 1 | 21.3 | 6.68 | 9.39 | 7.01 | 6.96 | 6.52 | 6.62 |
| Day 7 | 22.2 | 6.05 | 6.43 | 1.71 | 1.66 | 1.58 | 2.14 |
| Day 12 | 22.20 | 6.27 | 5.13 | 0.83 | 0.98 | 1.12 | 1.74 |

One then normalizes the $O_2$ concentration (5.70 represents no degradation, 0.91 represents complete degradation; use these values to determine what level of degradation 1.05 represents).

TABLE 32

Normalized oxygen concentration and Biodegradability %

| Samples | Measured $O_2$ Conc at Day 12 (mg/L) | Average $O_2$ Conc at Day 12 (mg/L) | Degradation | Degradation Index |
|---|---|---|---|---|
| River Water (no particles control) | 6.27 | 5.70 | No Degradation | 0% |
| Tap water + particles (no microbes control) | 5.13 | | | |
| River water + starch (complete biodegradation control) | 0.83 | 0.91 | Complete Degradation | 100% |
| River water + starch (complete biodegradation control) | 0.98 | | | |
| River water + particles of Example 4F | 1.12 | 1.43 | (5.70-1.43) | 89% |
| River water + particles of Example 4F | 1.74 | | (5.70-0.91) | |

89% represents the environmental degradability of the entire particle. If one were to just look at the environmental biodegradability of the encapsulation matrix (assume that the active material that is encapsulated is not degradable), that degradability is 99%.

While the invention has been described in detail and with reference to specific examples thereof, it will be apparent to one skilled in the art that various changes and modifications can be made therein without departing from the spirit and scope thereof.

What is claimed is:

1. A controlled release particle comprising 10-70 wt. % of a hydrophobic active ingredient, 21-72 wt. % of a polysaccharide, 3.80-12 wt. % of a crosslinking agent, 1.00-6 wt. % of a catalyst, 0.10-5 wt. % of a silica flow aid, and optionally 0.10 -5 wt. % of a desiccant, wherein the controlled release particle is anhydrous and the hydrophobic active ingredient is dispersed in a crosslinked polysaccharide matrix effective to retain the hydrophobic active ingredient upon exposure to water and effective to release the hydrophobic active ingredient in response to at least one of friction and enzymes.

2. The controlled release particle of claim 1, further comprising 1.05-3.30 wt. % of an epoxidized oil and 1.00-23 wt. % of an amine-functionality containing material selected from the group consisting of poly(diallyl dimethylammonium) halides, copolymers of poly(diallyl dimethylammonium) chloride and polyvinyl pyrrolidone, acrylamides, imidazoles, imidazolinium halides, polyvinyl amine, copolymers of polyvinyl amine and N-vinyl formamide, polyvinylformamide, copolymers of polyvinylamine and polvyinylalcohol oligimers of amines, diethylenetriamine, ethylene diamine, bis(3-aminopropyl)piperazine, N,N-bis-(3-aminopropyl)methylamine, tris(2-aminoethyl)amine, polyethyleneimime, ethoxylated polyethyleneimine, polybutadiene/styrene, polybutadiene/acrylonitrile, carboxyl-terminated polybutadiene/acrylonitrile, chitosan with various degrees of deacetylation, carboxymethyl chitosans, glycol chitosans, whey protein, sodium caseinate, silk protein, polyamines and mixtures thereof.

3. The controlled release particle of claim 1, wherein the hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

4. The controlled release particle of claim 1, wherein the polysaccharide is a member selected from the group consisting of octenyl succinic acid anhydride modified starch, gum arabic, xanthan gum, gellan gum, pectin gum, konjac gum and carboxyalkyl cellulose.

5. The controlled release particle of claim 1, wherein the crosslinking agent is a member selected from the group consisting of dimethyldihydroxy urea, dimethyldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(acrylic acid), poly(methacrylic acid), poly(maleic acid), poly(methylvinylether-co-maleate) copolymer, copolymers of acrylic acid and copolymers of maleic acid.

6. The controlled release particle of claim 1, wherein the catalyst is a member selected from the group consisting of ammonium chloride, ammonium sulfate, aluminum chloride, magnesium chloride, magnesium nitrate and sodium hypophosphite.

7. The controlled release particle of claim 1, wherein the silica flow aid is a member selected from the group consisting of fumed silica, precipitated silica, calcium silicate, aluminosilicate, and combinations thereof.

8. The controlled release particle of claim 1, which have a diameter from 0.1 microns to less than 100 microns.

9. The controlled release particle of claim 1, having an Environmental Degradability index greater than 80.

10. A method for preparing the controlled release particle of claim 1, said method comprising:
    mixing the hydrophobic active ingredient with the polysaccharide and water to provide an emulsion;
    agitating the emulsion to provide a modified emulsion containing hydrophobic active ingredient droplets with a volume average diameter of less than 5 microns;
    mixing with the modified emulsion the crosslinking agent and the catalyst to provide a spray-ready emulsion;
    spray drying the spray-ready emulsion to provide a powder;
    adding the silica flow aid to the powder to provide a modified powder; and
    heating the modified powder to form the controlled release particle.

11. A method for preparing the controlled release particle of claim 2, said method comprising:
    mixing the hydrophobic active ingredient with the epoxidized oil to provide a homogeneous solution;
    mixing the homogeneous solution with a polysaccharide solution comprising the polysaccharide, the crosslinking agent, the catalyst and water to provide an emulsion;
    agitating the emulsion to provide a modified emulsion containing hydrophobic active ingredient droplets with a volume average diameter of less than 5 microns;
    mixing with the modified emulsion the amine-functionality containing material to provide a spray-ready emulsion;
    spray drying the spray-ready emulsion to provide a powder;
    adding silica flow aid to the powder to provide a modified powder; and
    heating the modified powder to form the controlled release particle.

12. The method of claim 10, wherein the modified powder is heated within a temperature range of 130-185° C.

13. A composition comprising the controlled release particle of claim 1, wherein the composition is a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye and a unit dose detergent comprising a detergent and the controlled release particle in a water soluble film.

14. The composition of claim 13, further comprising at least one suspension agent to suspend the controlled release particle, wherein the at least one suspension agent is at least one member selected from the group consisting of a rheology modifier, a structurant and a thickener.

15. The composition of claim 14, wherein the at least one suspension agent has a high shear viscosity at, 20 sec$^{-1}$ shear rate and at 21° C., of from 1 to 7000 cps and a low shear viscosity, at 0.5 sec$^{-1}$ shear rate at 21° C., of greater than 1000 cps.

16. The composition of claim 14, which has a high shear viscosity, at 20 sec$^{-1}$ and at 21° C., of from 50 to 3000 cps and a low shear viscosity, at 0.5 sec$^{-1}$ shear rate at 21° C., of greater than 1000 cps.

17. The composition of claim 14, wherein the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, hydrogenated castor oil, hydrogenated castor wax and mixtures thereof.

18. The composition of claim 13, having at least two controlled release technologies, which release different hydrophobic oil compositions and are selected from the group consisting of neat oils, friction-triggered release microcapsules and water-triggered release microcapsules.

19. The controlled release particle claim 1, wherein the hydrophobic active ingredient comprises a mixture of a hydrophobic active and a material selected from the group consisting of plant waxes, animal waxes, petroleum based waxes, synthetic waxes, mineral waxes, brominated oils, hydrophobically modified inorganic particles, nonionic emulsifiers and oil thickening agents.

20. The controlled release particle claim 1, wherein the desiccant is a member selected from the group consisting of calcium sulfate, sodium sulfate, calcium silicate, hydrophilic aluminosilicates, magnesium sulfate, silica gel, crosslinked polyacrylates and combinations thereof.

21. The method of claim 12, wherein the modified powder is heated by using convective, conductive, or radiative heat transfer.

* * * * *